(12) United States Patent
Wang et al.

(10) Patent No.: US 7,629,330 B2
(45) Date of Patent: Dec. 8, 2009

(54) USE OF ZWITTERIONIC POLYSACCHARIDES FOR THE SPECIFIC MODULATION OF IMMUNE PROCESSES

(75) Inventors: Ying Wang, Brookline, MA (US); Michael H. Roehrl, Brookline, MA (US); Dennis L. Kasper, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 595 days.

(21) Appl. No.: 10/432,406

(22) PCT Filed: Dec. 5, 2001

(86) PCT No.: PCT/US01/47251

§ 371 (c)(1),
(2), (4) Date: Nov. 20, 2003

(87) PCT Pub. No.: WO02/45708

PCT Pub. Date: Jun. 13, 2002

(65) Prior Publication Data

US 2004/0092433 A1 May 13, 2004

Related U.S. Application Data

(60) Provisional application No. 60/251,747, filed on Dec. 5, 2000.

(51) Int. Cl.
*A01N 43/04* (2006.01)
*A61K 31/715* (2006.01)

(52) U.S. Cl. ..................... 514/54; 536/123.1
(58) Field of Classification Search ............... None
See application file for complete search history.

(56) References Cited

U.S. PATENT DOCUMENTS

| | | | |
|---|---|---|---|
| 5,331,573 A | 7/1994 | Balaji et al. | |
| 5,679,654 A | 10/1997 | Tzianabos et al. | |
| 5,700,787 A * | 12/1997 | Tzianabos et al. | 514/54 |
| 5,888,741 A | 3/1999 | Hendry | |
| 6,110,672 A | 8/2000 | Mandel et al. | |

FOREIGN PATENT DOCUMENTS

WO      WO 00/59515 A2    10/2000

OTHER PUBLICATIONS

Comstock et al. Journal of Bacteriology (1999), vol. 181, pp. 6192-6196.*
Brubaker et al. The Journal of Immunology (1999), vol. 162, pp. 2235-2242.*
Baumann H et al., "Structural elucidation of two capsular polysaccharides from one strain of *Bacteroides fragilis* using high-resolution NMR spectroscopy," *Biochemistry* (1992) 31:4081-89.
Brubaker JO et al., "Mitogenic activity of purified capsular polysaccharide A from *Bacteroides fragilis*: differential stimulatory effect on mouse and rat lymphocytes in vitro," *J. Immunol.* (1999) 162:2235-42.
Comstock LE et al., "Interstrain variation of the polysaccharide B biosynthesis locus of *Bacteroides fragilis*: characterization of the region from strain 638R," *J. Bacteriol.* (1999) 181:6192-96.
Coyne MJ et al., *Bacteroides fragilis* NCTC9343 produces at least three distinct capsular polysaccharides: cloning, characterization, and reassignment of polysaccharide B and C biosynthesis loci. *Infect Immun.* Nov. 2000;68(11):6176-81.
Dahiyat BI. et al., "De novo protein design: fully automated sequence selection," .*Science* (1997) 278:82-87.
Hirata N et al., "Cytokine synthesis of human monocytes stimulated by triple of single helical conformer of an antitumour (1→3)-beta-D-glucan preparation, sonifilan." *Zentralbl Bakteriol* (1998) 288:403-13. Abstract.
Kalka-Moll WM et al., "Effect of molecular size on the ability of zwitterionic polysaccharides to stimulate cellular immunity," *J. Immunol* (2000) 164:719-24.
Kulicke WM et al., "Correlation between immunological activity, molar mass, and molecular structure of different (1→3)-beta-D-glucans." *Carbohydr. Res* (1997) 297:135-43. Abstract.
Ohno N et al., "Enhancement of LPS triggered TNF-alpha (tumor necrosis factor-alpha) production by (1→3)-beta-D-glucans in mice." Biol. Pharm. Bull (1995) 18:126-33.
Ohno N et al., "Comparison of the immunopharmacological activities of triple and single-helical schizophyllan in mice." *Biol. Pharm Bull* (1995) 18:1242-47.
Pantosti A et al., "Immunochemical characterization of two surface polysaccharides of *Bacteroides fragilis*," *Infect Immun.* (1991) 59:2075-82.
Schneider G et al., "De novo design of molecular architectures by evolutionary assembly of drug-derived building blocks." *J. Computer-Aided Mol. Design* (2000) 14:487-94.
Stein KE, "Thymus-independent and thymus-dependent responses to polysaccharide antigens," *J. Infect. Dis* (1992) 165:S49-S52.
Tzianabos AO et al., "Structural features of polysaccharides that induce intra-abdominal abscesses," *Science* (1993) 262:416-19.
Tzianabos AO et al., "Polysaccharide-mediated protection against abscess formation in experimental intra-abdominal sepsis," *J Clin. Invest.* (1995) 96:2727-31.
Tzianabos AO et al., "Structural characteristics of polysaccharides that induce protection against intra-abdominal abscess formation," *Infect Immun* (1994) 62:4881-86.
Tzianabos AO et al., "T cells activated by zwitterionic molecules prevent abscesses induced by pathogenic bacteria," *J. Biol. Chem.* (2000) 275: 6733-40.

(Continued)

*Primary Examiner*—Patrick T Lewis
(74) *Attorney, Agent, or Firm*—Wolf, Greenfield & Sacks, P.C.

(57) ABSTRACT

The invention relates to three-dimensional molecular structure determination of polymers, three-dimensional computer molecular modeling, rational drug design, and immunomodulatory polymers. In particular the invention is directed to immunomodulatory polymers, as well as to methods for designing, selecting, and screening therapeutic agents having immunomodulatory activity.

2 Claims, 7 Drawing Sheets

OTHER PUBLICATIONS

Tzianabos AO et al., "The capsular polysaccharide of *Bacteroides fragilis* comprises two ionically linked polysaccharides," *J. Biol. Chem.* (1992) 267:18230-35.

Wang Y et al., "Structural basis of the abscess-modulating polysaccharide A2 from *Bacteroides fragilis*," *Proc Natl Acad Sci USA* (2000) 97:13478-83.

Wang Y et al., "Structure characterization of an abscessogenic capsular polysaccharide from *Bacteriodes fragilis* by NMR spectroscopy." IXI Int'l Conference of NMR in Biological Systems, Florence, Italy, Aug. 20-25, 2000. Abstract.

* cited by examiner

USE OF ZWITTERIONIC POLYSACCHARIDES FOR THE SPECIFIC MODULATION OF IMMUNE PROCESSES

FEDERALLY SPONSORED RESEARCH

This invention was made with Government support under National Institutes of Health Grant AI 39576. Accordingly, the Government has certain rights to this invention.

RELATED APPLICATIONS

This application is a national stage filing under 35 U.S.C. § 371 of International application PCT/US01/47251, filed Dec. 5, 2001, which was published in English under PCT Article 21(2), and claims priority under 35 U.S.C. §119(e) to U.S. provisional patent application Ser. No. 60/251,747, filed on Dec. 5, 2000.

FIELD OF THE INVENTION

The present invention is in the fields of biotechnology, three-dimensional molecular structure determination, three-dimensional computer molecular modeling, rational drug design, and immunomodulatory polymers. The invention is directed to immunomodulatory polymers, as well as to methods for designing, selecting, and screening therapeutic agents having immunomodulatory activity. The present invention also provides three-dimensional computer modeling of the polysaccharide PS A2 for rational drug design based on the use of nuclear magnetic resonance (NMR), chemical methods, and gas chromatography-mass spectroscopy data on computer readable media.

BACKGROUND OF THE INVENTION

*Bacteroides fragilis* species are obligate anaerobic Gram-negative bacteria and the most common anaerobes isolated from severe human infections, such as intraabdominal sepsis and abscesses. Gorbach S L et al. (1974) in *Anaerobic Microorganisms in Intraabdominal Infections* (Charles C. Thomas, Springfield, Ill.), pp. 399-407; Aldridge K E (1995) *Am J Surg* 169:2S-7S; Polk: B J et al. (1977) *Ann Intern Med* 86:567-71. Abscesses are a characteristic host response to infection by *B. fragilis* and cause considerable morbidity and mortality. Cross AS (1994) *Lancet* 343:248-9. Previous investigations in animal models have demonstrated that capsular polysaccharides (CPs) isolated from *B. fragilis* are capable of modulating the course of abscess formation via a T-cell-dependent mechanism. U.S. Pat. Nos. 5,679,654; 5,700,787; Brubaker J O et al. (1999) *J Immunol* 162:2235-42; Tzianabos A O et al. (1995) *Infect Immun* 62:4881-6; Tzianabos A O et al. (1995) *J Clin Invest* 96:2727-31; Kalka-Moll W M et al. (2000) *J Immunol* 164, 719-24; Tzianabos A O et al. (2000) *J Biol Chem* 275, 6733-40. More important, *B. fragilis* CPs can confer protection against a wide variety of abscess-inducing microorganisms, including *B. fragilis* itself, *Staphylococcus aureus*, *Streptococcus pneumoniae*, and other synergistic microbes. Brubaker J O et al. (1999) *J Immunol* 162:2235-42; Tzianabos A O et al. (1995) *Infect Immun* 62:4881-6; Tzianabos A O et al. (1995) *J Clin Invest* 96:2727-31; Kalka-Moll W M et al. (2000) *J Immunol* 164,719-24; Tzianabos A O et al. (2000) *J Biol Chem* 275, 6733-40. It is interesting to note that, in contrast to the paradigm that carbohydrate antigens are T-cell independent, *B. fragilis* CPs activate T cells to proliferate and elicit cytokine responses. Tzianabos A O et al. (2000) *J Biol Chem* 275, 6733-40; Stein K E (1992) *J Infect Dis* 165:S49.

Immunomodulating CPs from *B. fragilis* are structurally distinctive in that they are zwitterionic polysaccharides (ZPSs), carrying a high density of both positive and negative charges. Previous studies have identified two ZPSs, PS A (hereinafter PS A1) and PS B, from the capsule of *B. fragilis* 9343 (Pantosti A et al. (1991) *Infect Immun* 59:2075-82; Baumann H et al. (1992) *Biochemistry* 31:4081-9; Tzianabos A O et al. (1993) *Science* 262:416-9), both of which are potent activators of T cells in vitro and protect animals against abscess formation in vivo. Brubaker J O et al. (1999) *J Immunol* 162:2235-42; Tzianabos A O et al. (1995) *Infect Immun* 62:4881-6; Tzianabos A O et al. (1995) *J Clin Invest* 96:2727-31; Kalka-Moll W M et al. (2000) *J Immunol* 164, 719-24. The charges are critical determinants of immunologic activity, as chemical neutralization of these groups abolishes T-cell stimulation. Brubaker J O et al. (1999) *J Immunol* 162:2235-42; Tzianabos A O et al. (1995) *Infect Immun* 62:4881-6; Tzianabos A O et al. (1995) *J Clin Invest* 96:2727-31; Kalka-Moll W M et al. (2000) *J Immunol* 164, 719-24. More recent studies suggest that T-cell-mediated abscess modulation is a common property of ZPSs. Tzianabos A O et al. (2000) *J Biol Chem* 275, 6733-40.

Realizing that molecular charges of ZPSs are critical determinants of their immunological effects, while the primary structures of these compounds differ significantly, a need remains for understanding details of the structures of different ZPSs from various strains of *B. fragilis,* particularly as they may relate to the unique immunological properties of these polysaccharides.

SUMMARY OF THE INVENTION

The invention is based in part on the discovery that certain immunomodulating polymers possess characteristic three-dimensional features in addition to a requisite charge motif. The immunomodulating polymers can alter immune cell function by inducing cytokine production, e.g., interleukin 2 (IL-2) or interleukin 10 (IL-10); activating immune cells, such as T cells; and suppressing antigen-specific immunoglobulin G (IgG) antibody production.

In a first aspect the invention relates to an isolated immunomodulatory polymer, wherein the polymer comprises a plurality of a repeating unit, with each repeating unit comprising a tetramer backbone having a structure —($S_1$-$S_2$-$S_3$-$S_4$)— including, each independent of the others, a first subunit $S_1$, a second subunit $S_2$, a third subunit $S_3$, and a fourth subunit $S_4$, each tetramer backbone including a negatively charged moiety on the first subunit $S_1$ and a free amino moiety on the fourth subunit $S_4$. The immunomodulatory polymer in some embodiments is a naturally occurring polymer.

The negatively charged moiety on the first subunit in some embodiments is a carboxyl, a phosphate, or a phosphonate.

The subunits in various embodiments are any known type of polymer subunit. These subunits may include but are not limited to monosaccharides, disaccharides, amino acids, dipeptides, nucleotides, $C_{5-18}$ cycloalkyls, $C_{5-18}$ aryls, and combinations and analogs thereof. In one embodiment the subunits are independently monosaccharides or analogs thereof. In another embodiment the subunits are independently amino acids or analogs thereof. The subunits independently may be branched or unbranched, i.e., they may or may not include an appended subunit or other substituent that is not part of the backbone of the polymer. In some embodiments the subunits $S_3$ are branched.

The free amino moiety on the fourth subunit of one repeating unit, in some embodiments is less than about 32 Å from a next-nearest free amino moiety on the fourth subunit of another unit. Recognizing that a polymer may have primary, secondary and tertiary structure, the about 32 Å distance is to be understood to mean as measured along the backbone of the polymer, or, equivalently, as measured along the primary structure of the polymer. Likewise, the term "next-nearest" in this context means adjacent to, as determined along the backbone or primary structure. In addition, the about 32 Å distance is to be understood to mean as measured between the nitrogen of the free amino moiety on the fourth subunit of one repeating unit and the nitrogen of the free amino moiety on the next-nearest fourth subunit of another unit.

The invention in a second aspect relates to an isolated immunomodulatory polysaccharide, wherein the polysaccharide comprises a plurality of a repeating unit, with each repeating unit comprising a tetrasaccharide backbone having a structure —$(M_1$-$M_2$-$M_3$-$M_4)$— including, each independent of the others, a first monosaccharide $M_1$, a second monosaccharide $M_2$, a third monosaccharide $M_3$, and a fourth monosaccharide $M_4$, each tetrasaccharide backbone including a negatively charged moiety on the first monosaccharide $M_1$ and a free amino moiety on the fourth monosaccharide $M_4$. In some embodiments the immunomodulatory polysaccharide is a naturally occurring polysaccharide. In a preferred embodiment the immunomodulatory polysaccharide is polysaccharide PS A2 of *Bacteroides fragilis* 638R. The polysaccharide PS A2 is to be understood to be distinct from the polysaccharide PS A1.

According to some embodiments the negatively charged moiety on the first monosaccharide is selected from the group consisting of: carboxyl, phosphate, and phosphonate.

The monosaccharides of the polysaccharide may be independently monosaccharides or analogs thereof and may be branched or unbranched. In one embodiment the monosaccharide $M_3$ of the repeating unit is branched.

In some embodiments the free amino moiety on the fourth monosaccharide of one repeating unit is less than about 32 Å from a next-nearest free amino moiety on the fourth monosaccharide of another unit. The distance of less than about 32 Å and the next-nearest free amino moiety on the fourth monosaccharide of another unit are to be understood to mean as measured along the backbone or primary structure of the polysaccharide.

According to these first two aspects of the invention, in some embodiments the plurality of a repeating unit includes at least 3, at least 4, at least 5, at least 6, at least 7, at least 8, at least 9, at least 10, at least 15, and at least 20 repeating units. In certain embodiments the plurality of a repeating unit includes at least 3, at least 4, at least 5, at least 6, at least 7, at least 8, at least 9, at least 10, at least 15, and at least 20 contiguous repeating units. In some embodiments the immunomodulatory polymer or polysaccharide consists essentially of a plurality of the repeating unit. The repeating unit in certain embodiments is a pentamer; in certain embodiments the repeating unit is a branched pentamer.

The invention in a third aspect is a pharmaceutical preparation which activates immune cells. The pharmaceutical preparation according to this aspect is an effective amount, for activating immune cells, of an isolated immunomodulatory polymer according to the first aspect of the invention, and a pharmaceutically acceptable carrier.

The invention in a fourth aspect is a pharmaceutical preparation which activates immune cells. The pharmaceutical preparation according to this aspect is an effective amount, for activating immune cells, of an isolated immunomodulatory polysaccharide according to the second aspect of the invention, and a pharmaceutically acceptable carrier.

The invention in a fifth aspect is an isolated immunomodulatory polysaccharide comprising PS A2.

The invention in a sixth aspect provides a pharmaceutical preparation which activates immune cells. The pharmaceutical preparation according to this aspect is an effective amount, for activating immune cells, of an isolated immunomodulatory polysaccharide according to the fifth aspect of the invention, and a pharmaceutically acceptable carrier.

In some embodiments the polymer or polysaccharide of any of the foregoing pharmaceutical preparations is a modified form or derivative of a naturally occurring polymer or polysaccharide.

In a seventh aspect, the invention is an isolated immunomodulatory polymer, wherein the polymer includes a backbone having a plurality of a repeating charge motif, wherein the repeating charge is a positive charge and a negative charge arranged along the polymer so that positive charges of consecutive charge motifs are separated by less than about 32 Å, wherein the polymer has a three-dimensional solution conformation in which a majority of the positive charges and the negative charges are solvent-accessible, said three-dimensional solution conformation having a plurality of docking sites, each docking site being about 10 Å wide and about 5 Å deep.

The polymer according to this aspect of the invention may be any type of immunomodulatory polymer known in the art. In one embodiment the immunomodulatory polymer is a polysaccharide, such as PS A2. In other embodiments the immunomodulatory polymer is a polypeptide or a mixed polymer.

In a preferred embodiment according to this and each of the above aspects of the invention, the immunomodulatory polymer or polysaccharide is not PS A1, PS B, *Salmonella typhi* Vi antigen, *Escherichia coli* K5 antigen, *Staphylococcus aureus* type 5 capsular polysaccharide, *Rhizobium meliloti* exopolysaccharide II, group B *streptococcus* type III capsular polysaccharide, *Pseudomonas aerugenosa* Fisher immunotype 7O-antigen, *Shigella sonnei* Phase I lipopolysaccharide O-antigen, *Streptococcus pneumoniae* type I capsular polysaccharide, *Streptococcus pneumoniae* group antigen: C substance, or *Trypanosoma cruzi* lipopeptidophosphoglycan.

The polymer may include a plurality of a repeating unit. In some embodiments the plurality of a repeating unit of the polymer includes at least 3, at least 4, at least 5, at least 6, at least 7, at least 8, at least 9, at least 10, at least 15, and at least 20 repeating units. In other embodiments the plurality of a repeating unit includes at least 3, at least 4, at least 5, at least 6, at least 7, at least 8, at least 9, at least 10, at least 15, and at least 20 contiguous repeating units. In certain embodiments the immunomodulatory polymer consists essentially of a plurality of the repeating unit.

In some embodiments the positive charge of the charge motif is a free amino group. In some embodiments the negative charge of the charge motif is a carboxyl, a phosphate, or a phosphonate.

The three-dimensional solution conformation in some embodiments includes a helix. In a preferred embodiment the helix is a right-handed helix. In a preferred embodiment the helix has a pitch of about 20 Å.

The immunomodulatory polymer according to this aspect of the invention includes a docking site. The docking site in some embodiments is at least about 10 Å long. In some embodiments the docking site includes a plurality of solvent-accessible charges. In certain embodiments the docking site is constructed and arranged to bind, under physiologic conditions, an alpha helix of a polypeptide with an affinity of at least $10^{-3}$ $M^{-1}$, $10^{-6}$ $M^{-1}$, or $10^{-9}$ $M^{-1}$.

In some embodiments the alpha helix of the polypeptide that is bound by the docking site of the immunomodulatory polymer is an alpha helix of a major histocompatibility complex (MHC) molecule or an alpha helix of a T-cell antigen receptor.

According to yet another aspect the invention is a pharmaceutical preparation which activates immune cells. The pharmaceutical preparation includes an effective amount, for activating immune cells, of any of the immunomodulatory polymers according to the seventh aspect of the invention described above, and a pharmaceutically acceptable carrier.

The invention also provides methods of altering an immune response using the polymers of the invention. These methods include therapeutic methods such as the treatment or prevention of IL-2-responsive disorders, e.g., human immunodeficiency virus (HIV) infection, acquired immunodeficiency syndrome (AIDS), and cancer; abscess formation; adhesion formation, e.g., postoperative surgical adhesions; Th1-responsive disorders, e.g., insulin-dependent diabetes mellitus, experimental allergic encephalomyelitis, inflammatory bowel disease, and allograft rejection; inflammatory conditions, e.g., sepsis, inflammatory bowel disease, pelvic inflammatory disease (PID), urinary tract infections, cancer, adhesions; autoimmune disease; graft-versus-host disease, e.g., promoting allograft survival; psoriasis; acute glomerulonephritis; Goodpasture's syndrome; certain autoimmune arthritidies including rheumatoid arthritis; systemic lupus erythematosus (lupus); Sjögren's syndrome; autoimmune hemolytic anemia; idiopathic thrombocytopenic purpura (ITP); and certain forms of thyroiditis.

According to another aspect the invention is a method for inducing protection against abscess formation associated with infection. The method involves administering to a subject in need of such protection any of the pharmaceutical preparations of the invention in an amount effective to induce protection against abscess formation associated with infection.

In yet another aspect the invention relates to a method for reducing surgical adhesion formation occurring at a surgical site. The method involves administering to a subject in need of such treatment any of the pharmaceutical preparations of the invention in an amount effective to reduce surgical adhesion formation.

In a further aspect the invention provides a method for inducing IL-2 secretion. The method involves administering to a subject in need of such IL-2 secretion any of the pharmaceutical preparations of the invention in an amount effective to induce IL-2 secretion.

In another aspect the invention provides a method for inducing IL-10 secretion. The method involves administering to a subject in need of such IL-10 secretion any of the pharmaceutical preparations of the invention in an amount effective to induce IL-10 secretion.

According to yet another aspect the invention provides a system for selecting a candidate immunomodulatory polymer. The system according to this aspect of the invention includes a prediction module having an input to receive an input signal specifying primary structure of a candidate immunomodulatory polymer, logic to generate a three-dimensional solution conformation of the candidate immunomodulatory polymer, and an output to output a polymer signal specifying the three-dimensional solution conformation of the candidate immunomodulatory polymer; and an analysis module having an input to receive the polymer signal, logic to select a candidate immunomodulatory polymer if its three-dimensional solution conformation generated by the prediction module includes (i) a plurality of repeating units, (ii) a plurality of solvent-accessible charges, and (iii) a plurality of docking sites wherein each docking site is about 10 Å wide and about 5 Å deep, and an output to output an output signal specifying a candidate immunomodulatory polymer if the candidate immunomodulatory polymer is selected by the analysis module.

In one embodiment a selected candidate immunomodulatory polymer is made up of repeating units. The repeating units may be contiguous or may be separated by intervening sequence.

In some embodiments a selected candidate immunomodulatory polymer has a repeating charge motif, the repeating charge motif being a positive charge and a negative charge arranged along the backbone so that positive charges of consecutive charge motifs are separated by less than about 32 Å. In a preferred embodiment the positive charge of the charge motif is a free amino group. The negative charge of the charge motif, in some embodiments, may be a carboxyl, a phosphate, or a phosphonate.

A selected candidate immunomodulatory polymer in some embodiments has a three-dimensional solution conformation comprising a helix. In a preferred embodiment, the helix has a pitch of about 20 Å.

A selected candidate immunomodulatory polymer includes a docking site. The docking site in some embodiments is at least about 10 Å long. In other embodiments the docking site includes a plurality of solvent-accessible charges. In yet other embodiments the docking site is constructed and arranged to bind, under physiologic conditions, an alpha helix of a polypeptide with an affinity of at least $10^{-3}$ $M^{-1}$, $10^{-6}$ $M^{-1}$, or $10^{-9}$ $M^{-1}$.

In some embodiments the selected candidate immunomodulatory polymer has a sugar backbone. In some embodiments a selected candidate immunomodulatory polymer is a polysaccharide. In yet other embodiments a selected candidate immunomodulatory polymer has a polypeptide backbone.

In a further aspect the invention provides a computer-implemented method for selecting a candidate immunomodulatory polymer. The computer-implemented method according to this aspect of the invention involves receiving a signal specifying a primary structure of a candidate immunomodulatory polymer; generating a three-dimensional solution conformation of the candidate immunomodulatory polymer; selecting a candidate immunomodulatory polymer if the three-dimensional solution conformation of the candidate immunomodulatory polymer includes a plurality of repeating units, a plurality of solvent-accessible charges, and a plurality of docking sites, each docking site being about 10 Å wide and about 5 Å deep; and outputting an output signal specifying the candidate immunomodulatory polymer if the candidate immunomodulatory polymer is selected.

In one embodiment the signal specifying a primary structure of a candidate immunomodulatory polymer specifies a plurality of candidate immunomodulatory polymers.

In one embodiment a selected candidate immunomodulatory polymer is made up of repeating units. The repeating units can be contiguous or they can be separated by intervening sequence.

In some embodiments a selected candidate immunomodulatory polymer has a repeating charge motif, the repeating charge motif being a positive charge and a negative charge arranged along the backbone so that positive charges of consecutive charge motifs are separated by less than about 32 Å. In a preferred embodiment the positive charge of the charge motif is a free amino group. The negative charge of the charge motif, in some embodiments, may be a carboxyl, a phosphate, or a phosphonate.

A selected candidate immunomodulatory polymer in some embodiments has a three-dimensional solution conformation comprising a helix. In a preferred embodiment, the helix has a pitch of about 20 Å.

A selected candidate immunomodulatory polymer includes a docking site. The docking site in some embodiments is at least about 10 Å long. In other embodiments the docking site includes a plurality of solvent-accessible charges. In yet other embodiments the docking site is constructed and arranged to bind, under physiologic conditions, an alpha helix of a polypeptide with an affinity of at least $10^{-3}$ $M^{-1}$, $10^{-6} M^1$, or $10^{-9} M^1$.

In some embodiments the selected candidate immunomodulatory polymer has a sugar backbone. In some embodiments a selected candidate immunomodulatory polymer is a polysaccharide. In yet other embodiments a selected candidate immunomodulatory polymer has a polypeptide backbone.

The method in some embodiments also involves contacting a selected candidate immunomodulatory polymer with an immune cell, under physiologic conditions in which the immune cell is normally not activated, and measuring an activation marker of the immune cell.

In yet another aspect the invention provides a system for designing a candidate immunomodulatory polymer. The system according to this aspect of the invention includes a virtual subunit selection module having (a) an input to receive an input signal specifying a plurality of virtual subunits corresponding to chemical compounds, the plurality of virtual subunits including virtual subunits having positive charge, virtual subunits having negative charge, and virtual subunits having no charge, wherein each virtual subunit comprises a core and optionally at least one charged or neutral substituent attached to the core, (b) logic for selecting from the plurality of virtual subunits (i) a virtual subunit having positive charge, (ii) a virtual subunit having a negative charge, or (iii) both (i) and (ii), and (c) an output to output a selected virtual subunit signal; a conversion module having a first input to receive the selected virtual subunit signal and a second input to receive an input signal specifying at least one template, wherein the template is a three-dimensional solution phase representation of a reference immunomodulatory polymer having a plurality of repeating units, each unit comprising a charge motif provided by at least a first subunit having a positive charge and a second subunit having a negative charge, logic to convert (i) the subunit having the positive charge of the charge motif of the template with the virtual subunit having positive charge selected from the plurality of virtual subunits, (ii) the subunit having negative charge of the charge motif of the template with the virtual subunit having a negative charge selected from the plurality of virtual subunits, or (iii) both (i) and (ii), and an output to output a converted template signal specifying a primary structure of a candidate immunomodulatory polymer; a prediction module having an input to receive the converted template signal, logic to generate a three-dimensional solution conformation of the candidate immunomodulatory polymer, and an output to output a polymer signal specifying the three-dimensional solution conformation of the candidate immunomodulatory polymer, and a comparison module having a first input to receive the polymer signal, a second input to receive the input signal specifying at least one template, and a third input to receive an input signal specifying comparison criteria selected to measure similarity between the polymer signal and the template, logic to compare the polymer signal and the template according to the comparison criteria, and an output to output an output signal specifying the candidate immunomodulatory polymer if comparison of the polymer signal and the template meets the comparison criteria.

According to yet another aspect the invention provides a computer-implemented method for designing a candidate immunomodulatory polymer. The computer-implemented method involves receiving a signal specifying a plurality of virtual subunits corresponding to chemical compounds, the plurality of virtual subunits including virtual subunits having positive charge, virtual subunits having negative charge, and virtual subunits having no charge, wherein each virtual subunit comprises a core and optionally at least one charged or neutral substituent attached to the core; selecting from the plurality of virtual subunits (i) a virtual subunit having positive charge, (ii) a virtual subunit having a negative charge, or (iii) both (i) and (ii); receiving a signal specifying at least one template, wherein the template is a three-dimensional solution phase representation of a reference immunomodulatory polymer having a plurality of repeating units, each unit comprising a charge motif provided by at least a first subunit having a positive charge and a second subunit having a negative charge; generating a candidate immunomodulatory polymer having a primary structure by converting (i) the subunit having the positive charge of the charge motif of the template with the virtual subunit having positive charge selected from the plurality of virtual subunits, (ii) the subunit having negative charge of the charge motif of the template with the virtual subunit having a negative charge selected from the plurality of virtual subunits, or (iii) both (i) and (ii); generating a three-dimensional solution conformation of the candidate immunomodulatory polymer having a primary structure; receiving a signal specifying comparison criteria selected to measure similarity between the three-dimensional solution conformation of the candidate immunomodulatory polymer and the template; comparing the three-dimensional solution conformation of the candidate immunomodulatory polymer and the template according to the comparison criteria; and outputting a signal specifying the candidate immunomodulatory polymer if comparison of the three-dimensional solution conformation of the candidate immunomodulatory polymer and the template meets the comparison criteria.

In one embodiment the reference immunomodulatory polymer is PS A2.

In some embodiments the candidate immunomodulatory polymer includes a polysaccharide; in some embodiments the candidate immunomodulatory polymer is a polysaccharide. In some embodiments the candidate immunomodulatory polymer includes a polypeptide; in some embodiments the candidate immunomodulatory polymer is a polypeptide.

The invention also includes in some aspects methods of manufacture of medicaments using the immunomodulating polymers of the invention. The methods involve placing an immunomodulating polymer of the invention in a pharmaceutically acceptable carrier. For instance, the invention includes methods for manufacturing a medicament useful in methods of treating or preventing IL-2-responsive disorders, e.g., HIV infection, AIDS, cancer, abscess formation, adhesion formation, e.g., postoperative surgical adhesions, Th1-responsive disorders, e.g., insulin-dependent diabetes mellitus, experimental allergic encephalomyelitis, inflammatory bowel disease, allograft rejection; inflammatory conditions, e.g., sepsis, inflammatory bowel disease, PBD, urinary tract infections, cancer, adhesions; autoimmune disease, graft-versus-host disease, e.g., promoting allograft survival; psoriasis; acute glomerulonephritis; Goodpasture's syndrome; certain autoimmune arthritidies including rheumatoid arthritis; lupus; Sjögren's syndrome; autoimmune hemolytic anemia; ITP; and certain forms of thyroiditis.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Definitions

Figure 1:
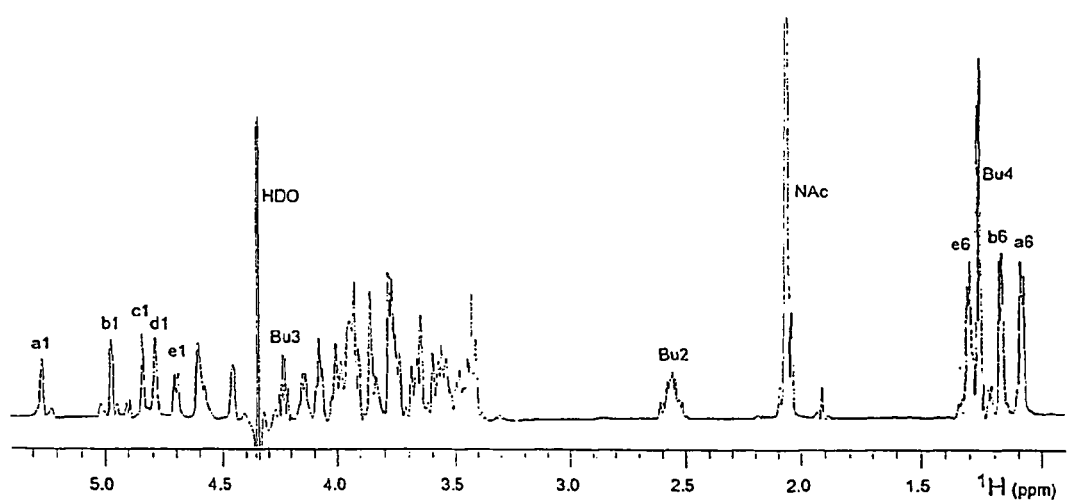
FIG. 1 is a graph depicting the $^1$H NMR spectrum of PS A2 recorded at 70° C.

The term "charge motif" as used herein refers to a positively charged free amino moiety and a negatively charged moiety. The negatively charged moiety may be selected from the group consisting of: carboxyl, phosphate, phosphonate, sulfate, and sulfonate.

The term "docking site" as used herein refers to a physical feature or region of a molecule which is involved in effecting and/or stabilizing a non-random intermolecular contact interaction with another molecule. Typically it involves an indentation or groove in the outer surface of the molecule.

The term "immune cell" refers to a cell of the immune system. Immune cells include T lymphocytes (T cells), B lymphocytes (B cells), granulocytes, monocytes, macrophages, natural killer (NK) cells, dendritic cells, and precursors thereof. Immune cells may be activated or quiescent, and there are various characteristics of activated immune cells, depending on their type and stimulus. An activated immune cell is a cell of the immune system that is stimulated to proliferate, mount or be ready to mount a protective response, or increase expression of a cell surface molecule or secreted molecule in response to contact with an antigen or other immune stimulus. A substance which activates immune cells is a substance that induces a quiescent or resting immune cell to become an activated immune cell. Activated immune cells may elaborate certain secreted products, for example, cytokines, chemokines, growth factors, antibodies (immunoglobulins), and small molecules (e.g., nitric oxide, NO). Cytokines include, without limitation, interleukin (IL)-1, IL-2, IL-3, IL-4, IL-5, IL-6, IL-7, IL-8, IL-10, IL-12, IL-15, IL-18, interferon (IFN)-α, IFN-β, IFN-γ, transforming growth factor (TGF)-β, tumor necrosis factor (TNF)-α, TNF-β, and granulocyte-macrophage colony-stimulating factor (GM-CSF). Immune cells may also upregulate certain molecules on their cell surface upon activation, for example, MHC class I, MHC Class II, CD11b, CD20, CD25, CD28, CD40, CD43, CD54, CD62L, CD69, CD71, CD80, CD86, CD95L, CD106, CD134, and CD134L. Methods for measuring immune activation markers are well known by those of ordinary skill in the art, including enzyme-linked immunosorbent assay (ELISA), fluorescence-activated cell sorting (FACS), bioassay, immunoblotting, immunoaffinity assay, reverse transcriptase/polymerase chain reaction (RT/PCR), and the like.

The term "immunomodulatory polymer" refers to a polymer which, when contacted with a cell of the immune system or a cell in fluid communication with a cell of the immune system, induces a change in the activation state of the immune cell. For example an immune cell may secrete a cytokine or antibody, or express a cell surface antigen, in response to such exposure to an immunomodulatory polymer. As suggested above, the change in the activation state of the immune cell may be direct or indirect. The polymer may be a homopolymer or a heteropolymer with respect to the class of subunits from which it is constructed. For example, one class of subunits includes monosaccharides; other examples of classes of subunits include amino acids, nucleotides, nucleosides, $C_{5-18}$ cycloalkyl, $C_{5-18}$ aryl, substituted derivatives, and analogs thereof The polymer may be a homopolymer or, preferably, a heteropolymer with respect to the individual subunits from which it is constructed. For example, a heteropolymer composed of monosaccharides may include a plurality of individual monosaccharide subunits, of which many are well known in the art.

Monosaccharides are carbohydrates that cannot be hydrolyzed to simpler compounds. Disaccharides are carbohydrates that can be hydrolyzed to two monosaccharides. Non-limiting examples of individual monosaccharide subunits may include fucopyranose, fucose, fucosamine, galactosamine, galactosaminuronic acid, galactose, galacturonic acid, gluconic acid, glucosamine, glucose, glucuronic acid, mannoheptose, mannonic acid, mannosamine, mannosaminuronic acid, mannose, mannuronic acid, and isomers and derivatives thereof.

Amino acids are monomers from which polypeptides are derived. Amino acids include but are not limited to natural amino acids. Natural amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

The term "intervening sequence" refers to chemical moieties occurring along the backbone of the polymer but extrinsic to the repeating units of the polymer. Intervening sequence may include, for example, at least one monosaccharide, cycloalkyl, or other chemically suitable moiety bridging two repeating units in a polysaccharide, where the repeating units are saccharides or oligosaccharides. As another non-limiting example, intervening sequence may include at least one amino acid, amino acid analog, or other chemically suitable moiety bridging two oligopeptide units forming a polypeptide.

The term "physiologic conditions" means conditions suitable for the maintenance of living cells. Physiologic conditions include in vivo and in vitro conditions. Typically physiologic conditions includes conditions of temperature, humidity, ionic strength, pH, oxygenation, and nutrients that are suitable for the maintenance of living cells.

The term "polysaccharide" refers to polymeric forms of aldo- or keto-hexose, pentose, and/or heptose monosaccharides and their derivatives. The monosaccharides are joined by glycoside linkages. Preferably the polysaccharide can be formed of repeating units of a maximum of ten monosaccharides, wherein each repeating unit includes at least one free amino moiety and one negatively charged moiety selected from the group consisting of: carboxyl, phosphate, phosphonate, sulfate, and sulfonate. More preferably the polysaccharide is formed of repeating units of a maximum of five monosaccharides. One such polysaccharide, the most preferred, is polysaccharide A2 (PS A2) of the *B. fragilis* capsular polysaccharide complex, described herein. Polysaccharides useful according to the present invention include the requisite charged groups. These polysaccharides may be derived from bacterial or other naturally occurring sources (e.g., seaweed, or they may be modified polysaccharides derived from naturally occurring sources, or they may be synthetic polysaccharides. Of note, the polysaccharides may be branched polysaccharides. Bacteria used as starting materials to obtain capsular polysaccharides can be obtained commercially from a number of sources. For example, the *B. fragilis*, NCTC 9343 and ATCC 23745 may be obtained from the National Collection of Type Cultures (London, England) and the American Type Culture Collection (Bethesda, Md.). Methods for purifying polysaccharide A and polysaccharide B from the above bacteria have been described. Pantosti A et al. (1991) *Infect Immun* 59:2075-82; Tzianabos A O et al. (1992) *J Biol Chem* 267:18230-5; U.S. Pat. No. 5,679,654 issued to Tzianabos et al. Capsular polysaccharides can be obtained in pure form from commercial sources including the ATCC.

Naturally occurring polysaccharides may be modified to selectively add, subtract, or modify various moieties, including free amino moieties, negatively charged moieties, or other moieties. Examples include adding free amino moieties by modifying existing N-acetyl groups or imine groups or forming hydroxymethyl groups from alcohol groups.

Thus, in addition to the naturally occurring polysaccharides, polysaccharide repeating units that consist of at least one N-acetyl sugar and at least one uronic acid (sugar with a negatively charged carboxyl group) can be modified to produce the immunomodulators of the present invention. A polysaccharide repeating unit containing at least one N-acetyl sugar and at least one uronic acid can be de-N-acetylated to create a free amino group and thus will yield a polysaccharide with the correct charge motif. Molecules which may be de-N-acetylated include *Salmonella typhi* capsular polysaccharide (Vi antigen), *Escherichia coli* K5 capsular polysaccharide, *Staphylococcus aureus* type 5 capsular polysaccharide, and *Rhizobium meliloti* exopolygaccharide II.

For those polysaccharides that contain imine moieties (C=NH), free amino groups can be formed by conventional chemistry techniques known to those of ordinary skill in the art. One suitable method involves the use of sodium borohydride ($NaBH_4$) to reduce the imine groups to free amino groups. This is done by adding in excess of 5 mg of borohydride to polysaccharide dissolved in distilled water while stirring at room temperature for 2 hours. The mixture is then dialyzed against water and freeze dried. DiFabio J L et al. (1989) *Can J Chem* 67:877-82.

De-N-acetylation can be accomplished by conventional chemistry techniques well known to those of ordinary skill in the art. One suitable method involves the use of alkali with or without sodium borohydride. Twenty mg of polysaccharide is dissolved in 2M NaOH (3 ml) and sodium borohydride is added (50 mg). The solution is heated to 100° C. for 5 hours. Following neutralization with acid, the solution is dialyzed against distilled water in the cold and freeze-dried. DiFabio J L et al. (1989) *Can J Chem* 67:877-82.

The term "PS A2" refers to the predominant polysaccharide occurring in the complex capsule of the genetically well-characterized strain *B. fragilis* 638R. The polysaccharide PS A2 is described in further detail herein.

The term "solvent-exposed surface" refers to the surface topology of a three-dimensional solution phase conformation of a molecule, where a subunit or residue of the molecule is said to be solvent-exposed if it has greater overall contact with solvent in which the molecule exists (or would exist) than it has to other subunits or residues of the molecule.

The term "subject" refers to a vertebrate, including humans, primates, horses, cows, sheep, pigs, goats, fowl, dogs, cats, rabbits, guinea pigs, and rodents.

The term "subunit" refers to a chemical compound or moiety, which chemical compound or moiety can participate in the formation of, or form the basis of, a polymer. Subunits may themselves be units of a polymer, or they may in combination contribute to the formation of larger units of a polymer. Typically a subunit is a chemical moiety or radical other than a single atom. For example, a subunit may be a monosaccharide, an amino acid, a nucleotide or nucleoside, a $C_{5-18}$ cycloalkyl, or $C_{5-18}$ aryl, and analogs thereof. Subunits may be combined according to rules of chemistry to form units (see below). For example monosaccharide subunits may be combined to form oligosaccharides; amino acid subunits may be combined to form oligopeptides, etc.

The term "three-dimensional solution conformation" refers to the group-level or, preferably, atomic-level distribution in three-dimensional space assumed by a molecule (or plurality of molecules) when it is in solution. Preferably the solution is an aqueous solution. The term refers to both the actual conformation in nature and any corresponding model representation, including in silico representation, of the molecule(s) in solution. Typically a three-dimensional solution conformation is determined through a combination of experimental chemical and physical measurements and, optionally, computer modeling. The computer modeling may include methods directed to energy minimization through iterative calculations which take into account such variables as torsional and rotational bond angle strain energies, electrostatic interactions, and energies of solvation. This term in most instances corresponds to what is ordinarily meant by secondary, tertiary and/or quaternary structure of the molecule(s), as these terms are used by those of ordinary skill in the art. The solution structure may differ from a corresponding crystal structure due, for example, to differences in intramolecular and intermolecular forces involved in solvation versus crystallization.

The term "unit" refers, in the context of a polymer, to a building block of the polymer. A unit may typically include a plurality of subunits. According to preferred embodiments of the instant invention, a unit maybe a repeating unit, i.e., the polymer contains a plurality of a particular unit. A unit includes elements that contribute to the formation of the backbone of the polymer. The backbone can include, for example, a polysaccharide, a polypeptide, a polynucleotide, and analogs and combinations thereof In preferred embodiments the backbone of the polymer is unbranched, i.e., the units are linked together in a linear manner, although individual subunits may include side chain substituents and the three-dimensional conformation of the polymer is nonlinear. For example, units of a polymer may be oligosaccharides joined end-to-end to form a polymer having an overall conformation of a helix. As another example, units of a polymer may be oligopeptides joined end-to-end to form a polymer having an overall conformation of a helix. The units may be the same or different, so long as they are building blocks of the polymer.

The term "virtual subunit" refers to a physically meaningful representation of a chemical compound or moiety, which chemical compound or moiety can participate in the formation of, or form the basis of, a chemical polymer. In a preferred embodiment, a virtual subunit is a computer representation of a chemical moiety as defined above. Such representation includes sufficient information about the chemical moiety so represented as to specify at least the overall two-dimensional, and more preferably, the overall three-dimensional features of the chemical moiety, as well as at least one chemically meaningful point of attachment through which the chemical moiety can be joined, through a covalent or hydrogen bond, to another virtual subunit. In more preferred embodiments the representation includes detailed information about the identities and relative positions of at least every non-hydrogen atom in the virtual subunit. Thus, for example, if a virtual subunit were a representation of the monosaccharide α-D-(+)-glucose, the representation corresponding to the virtual subunit would include at least the following information: a six-membered boat- or chair-shaped ring including an oxygen and five carbon atoms ($C_1$-$C_5$), a sixth carbon atom $C_6$ in an equatorial position attached to $C_5$ of the ring (adjacent to the oxygen of the ring), and five alcoholic hydroxy groups positioned as follows: equatorially on $C_2$, $C_3$, $C_4$, axially on $C_1$, and on $C_6$; the bond lengths between all joined non-hydrogen atoms; and the bond angles between all joined non-hydrogen atoms. See, for example, Morrison and Boyd, *Organic Chemistry* 3rd ed. (1973) Allyn and Bacon, Boston.

A virtual subunit may include a core component as well as at least one substituent. The core and/or the substituent may be uncharged or may include a free positive charge or free negative charge. A core component corresponds to an unsubstituted chemical moiety, for example a monosaccharide like glucose. A substituent corresponds to a chemical radical that can be added to or substituted for another radical of a suitable core component, for example, a carboxyl group or an amino group to form glucuronic acid or glucosamine from the core monosaccharide glucose. Any example above is provided for illustrative purposes alone and is in no way meant to be limiting.

It has been discovered according to the invention that certain immunomodulating polymers, useful for manipulating immune cells and for treating several types of immune-related disorders, possess characteristic three-dimensional features in addition to a requisite charge motif. The immunomodulating polymers described herein can alter immune cell function e.g., by inducing IL-2 production, inducing IL-10 production, activating T cells, and suppressing antigen-specific IgG antibody production. The group of compounds which are the immunomodulating polymers preferably have, in addition to a plurality of a charge motif characterized by a positively charged free amino group and a negatively charged group, a docking site constructed and arranged to bind an alpha helix of a polypeptide with an affinity of at least $10^{-3}$ $M^{-1}$. It is believed that the combination of charge distribution and docking sites on the immunomodulatory polymers stabilizes an interaction between the polymers and an alpha helix of a cell surface molecule of an immune cell. In particular, it is believed that the combination of structural and charged features of the polymer stabilizes an interaction between the polymer and an alpha helix of a major histocompatibility (MHC) molecule.

The invention relates in part to certain compositions that are immunomodulating polymers and methods of use thereof. Thus in one aspect the invention is a composition that is an immunomodulatory polymer comprising a plurality of a repeating unit, with each repeating unit comprising a tetramer backbone having a structure

-($S_1$-$S_2$-$S_3$-$S_4$)- including, each independent of the others, a first subunit $S_1$, a second subunit $S_2$, a third subunit $S_3$, and a fourth subunit $S_4$, each tetramer backbone including a negatively charged moiety on the first subunit $S_1$ and a free amino moiety on the fourth subunit $S_4$. In certain embodiments the immunomodulatory polymer includes a number of copies of the repeating unit structure above, wherein the number is an integer that is at least 3, at least 4, at least 5, at least 6, at least 7, at least 8, at least 9, at least 10, at least 15, at least 20, and any integer therebetween. According to these embodiments at least some of the repeated units may be joined by some intervening sequence that is extrinsic to the repeating unit. In certain embodiments the immunomodulatory polymer includes the structure -($S_1$-$S_2$-$S_3$-$S_4$)$_n$- wherein n is an integer that is at least 3, at least 4, at least 5, at least 6, at least 7, at least 8, at least 9, at least 10, at least 15, at least 20, and any integer therebetween. According to these embodiments the repeating units occur contiguously. In some embodiments the polymer is essentially entirely made up of the repeating unit.

The immunomodulatory polymer includes a negatively charged moiety associated with the first subunit. Preferably the negatively charged moiety is selected from the group consisting of: carboxyl, phosphate, and phosphonate, while others which may be selected can include sulfate and sulfonate.

The subunits of the polymer (e.g., $S_1$, $S_2$, $S_3$, $S_4$ ... etc.) are independently selected from the group consisting of: monosaccharide, disaccharide, amino acid, dipeptide, nucleotide, $C_{5-18}$ cycloalkyl, $C_{5-18}$ aryl, and combinations and analogs thereof Thus, for example, $S_1$, $S_2$, $S_3$, and $S_4$ could be independently selected as monosaccharides, provided $S_1$ and $S_4$ carry the requisite negative and positive charges. Likewise, for example, $S_1$, $S_3$, and $S_4$ could be independently selected as monosaccharides, and $S_2$ could be selected as a nonsugar $C_{5-18}$ cycloalkyl (e.g., cyclohexanyl, cyclohexanol) or $C_{5-18}$ aryl (e.g., benzyl).

In addition to naturally occurring subunits, the subunits may be analogs of naturally occurring subunits. For example, analogs of monosaccharides include such as carbamoylmethyl benzoic acid. See, for example, Mallaise W J (1999) *Exp Clin Endocrinol Diabetes* 107 Suppl 4:S140-3. Analogs of amino acids are well known in the art, e.g., peptoids (Simon R J et al. (1992) *Proc Natl Acad Sci USA* 89:9367-71), as are analogs of nucleotides, e.g., subunits forming peptide nucleic acids (also called polyamide nucleic acids; Uhlmann E (1998) *Biol Chem* 379:1045-52).

The immunomodulatory polymer may include subunits which are branched or unbranched. Thus for example, in addition to the four subunits shown above in the repeating unit, a further subunit could be attached to one of the four subunits shown. The unit could then have a structure including any one of the following:

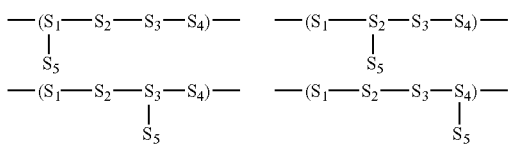

The examples shown above include various pentamers, where $S_5$ is a subunit as previously defined and may be selected independently of any other subunit. Further substituents $S_x$ may also be included, provided the unit structure and charge motif are maintained. A preferred branched pentamer unit is

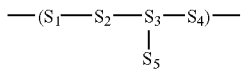

wherein the subunit $S_3$ is branched.

In certain embodiments the free amino moiety on the fourth subunit of one repeating unit is less than about 32 Å from a next-nearest free amino moiety on the fourth subunit of another unit.

The invention also relates in part to certain compositions that are one type of polymer, immunomodulating polysaccharides and methods of use thereof. It has been discovered that the polysaccharide PS A2 of *Bacteroides fragilis* 638R is immunomodulatory and that it has a highly ordered structure both in terms of its distribution of charges and in terms of its three-dimensional solution conformation. Both these features are believed to contribute to the immunomodulating effects of the polysaccharide. As presented below, PS A2 is based on a repeating unit containing five saccharide subunits abbreviated as a-e, the subunits being (a) 2-amino-4-acetamido-2,4,6-trideoxy-α-galactose; (b) α-L-fucopyranose; (c) mannoheptose, substituted with 3-hydroxybutanoic acid (Bu) through an ether linkage between the C3 of Bu and C6 of mannoheptose; (d) N-acetylmannosamine; and (e) 3-acetamido-3,6-dideoxyglucose. The saccharide subunits are linked as follows to form a pentasaccharide repeating unit: →2-c-(1→3)-d-(1→4)[b-(1→2)]-e-(1→3)-a-(1→. The structure of the unit can also be represented as

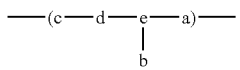

Figure 4:
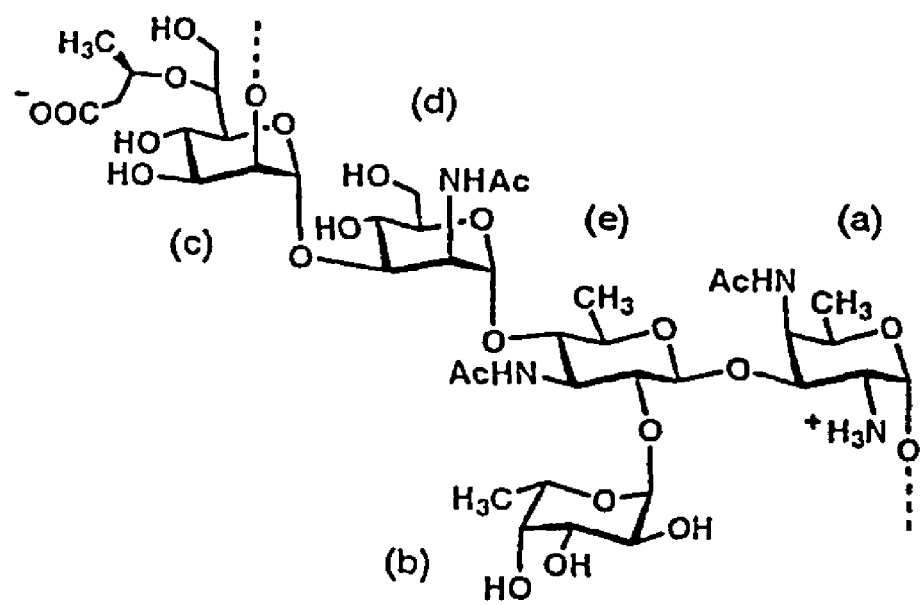
FIG. 4 is a graphic depicting the chemical structure of one repeating unit of PS A2.

According to this structure, c has a free carboxyl and a has a free amino group associated (see also FIG. 4). The repeat unit thus includes a charge motif which is a free amino group and a free negative charge, in this instance a carboxyl group.

Furthermore, the three-dimensional solution conformation of PS A2 was shown according to the instant invention to be a helix with a pitch of 20 Å and two repeating units per turn of the helix. The solution conformation of PS A2 is further characterized by the exposure of all the positive and negative charges on the outer surface of the polymer in a regularly spaced pattern, which renders them easily accessible to other molecules. The helix is further characterized by repeated large grooves whose lateral boundaries are occupied by the charges. The repeated grooves include docking sites, 10 Å wide, 5 Å deep, and 10 Å long, believed to accommodate an alpha helix of a polypeptide.

Thus in some aspects, the immunomodulating polymer is an immunomodulatory polysaccharide. The immunomodulatory polysaccharide may comprise a plurality of a repeating unit, with each repeating unit comprising a tetrasaccharide backbone having a structure

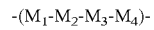

including, each independent of the others, a first monosaccharide $M_1$, a second monosaccharide $M_2$, a third monosaccharide $M_3$, and a fourth monosaccharide $M_4$, each tetrasaccharide backbone including a negatively charged moiety on the first monosaccharide $M_1$ and a free amino moiety on the fourth monosaccharide $M_4$. In certain embodiments the immunomodulatory polysaccharide includes a number of copies of the repeating unit structure above, wherein the number is an integer that is at least 3, at least 4, at least 5, at least 6, at least 7, at least 8, at least 9, at least 10, at least 15, at least 20, and any integer therebetween. According to these embodiments at least some of the repeated units may be joined by some intervening sequence that is extrinsic to the repeating unit. In certain embodiments the immunomodulatory polysaccharide includes the structure

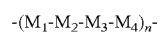

wherein n is an integer that is at least 3, at least 4, at least 5, at least 6, at least 7, at least 8, at least 9, at least 10, at least 15, at least 20, and any integer therebetween. According to these embodiments the repeating units occur contiguously. In some embodiments the polysaccharide is essentially entirely made up of the repeating unit.

The immunomodulatory polysaccharide according to this aspect of the invention includes a negatively charged moiety associated with the first monosaccharide. Preferably the negatively charged moiety is selected from the group consisting of: carboxyl, phosphate, and phosphonate, while others which may be selected can include sulfate and sulfonate.

The subunits are independently selected from monosaccharides and analogs thereof. Thus, for example, $M_1$, $M_2$, $M_3$, and $M_4$ could be independently selected as monosaccharides, provided $M_1$ and $M_4$ carry the requisite negative and positive charges. Likewise, for example, $M_1$, $M_3$, and $M_4$ could be independently selected as monosaccharides, and $M_2$ could be selected as a monosaccharide analog. As mentioned above, analogs of monosaccharides include, for example, carbamoylmethyl benzoic acid. Mallaise W J (1999) *Exp Clin Endocrinol Diabetes* 107 Suppl 4:S140-3.

Further, the immunomodulatory polysaccharide may include monosaccharides which are branched or unbranched. Thus for example, in addition to the four monosaccharides shown above in the repeating unit, a further monosaccharide could be attached to one of the four monosaccharides shown. The unit could then have a structure including any one of the following:

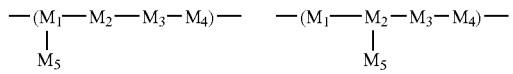

-continued

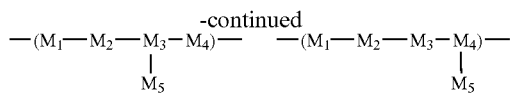

The examples shown above include various pentasaccharides, where $M_5$ is a monosaccharide as previously defined and may be selected independently of any other monosaccharide. Further substituents $M_x$ may also be included, provided the unit structure and charge motif are maintained. A preferred branched pentasaccharide unit is

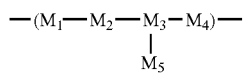

wherein the monosaccharide $M_3$ is branched. In a preferred embodiment the immunomodulatory polysaccharide is PS A2.

The free amino moiety on the fourth monosaccharide of one repeating unit may be less than about 32 Å from a next-nearest free amino moiety on the fourth monosaccharide of another unit.

The invention also relates in part to an isolated immunomodulating polysaccharide that comprises PS A2. As used herein, the term "isolated", with reference to a substance, means removed from its natural environment including other cell components. Thus "isolated" refers in this context to an immunomodulating polysaccharide removed from its natural environment including other cell components. An isolated substance need not necessarily be pure, i.e., an isolated substance can be admixed with other substances, provided it is removed from its natural environment.

Some of the immunomodulatory polymers have certain three-dimensional characteristics in aqueous solution phase. The three-dimensional characteristics include (i) a backbone having a plurality of a repeating charge motif, the repeating charge motif being a positive charge and a negative charge arranged along the backbone; (ii) a three-dimensional solution conformation in which at least a majority of the positive charges and the negative charges are solvent-accessible; and (iii) a plurality of docking sites, each docking site being about 10 Å wide and about 5 Å deep.

The arrangement of positive charges of consecutive charge motifs may be separated by less than about 32 Å. This property refers to their arrangement as measured along an essentially linearized primary structure as would be permitted by the backbone. In other words, the separation of less than about 32 Å describes a maximum distance of separation which will not be exceeded by any primary, secondary, or tertiary structure based on the primary structure.

In some embodiments the docking site is at least about 10 Å long. It is believed that both charge and conformation are important to the immunomodulatory function, and in preferred embodiments the docking site includes a plurality of solvent-accessible charges (thus, charged moieties that are on or near the outer surface of the molecule and oriented toward the solvent such that they are "solvent exposed").

The docking sites are preferably constructed and arranged to bind, under physiologic conditions, an alpha helix of a polypeptide with an affinity of at least $10^{-3}$ $M^{-1}$. More preferably, the docking sites are constructed and arranged to bind, under physiologic conditions, an alpha helix of a polypeptide with an affinity of at least $10^{-6}$ $M^{-1}$. Even more preferably, the docking sites are constructed and arranged to bind, under physiologic conditions, an alpha helix of a polypeptide with an affinity of at least $10^{-9}$ $M^{-1}$. In particularly preferred embodiments, the alpha helix so bound to the polymer is an alpha helix of a surface molecule on an immune cell. In a highly preferred embodiment, the alpha helix so bound to the polymer is an alpha helix of an MHC molecule, e.g., a class II MHC molecule, on the surface of an immune cell. In another highly preferred embodiment, the alpha helix so bound to the polymer is an alpha helix of a T-cell antigen receptor. The T-cell antigen receptor includes, but is not limited to, the αβ or γδ chains. It is well known by those of ordinary skill in the art that certain accessory molecules associate with the αβ or γδ heterodimers and are considered part of the T-cell receptor, including, for example, those contributing to the CD3 complex, e.g., γ, δ, ε, ζ, and η chains. The ability of a particular docking site to bind to an alpha helix and the strength of that binding interaction may be assessed using routine methods in the art, such as the methods described in the Examples below.

The immunomodulatory polymers may include a plurality of repeating units, including, for example, at least 3, at least 4, at least 5, at least 6, at least 7, at least 8, at least 9, at least 10, at least 15, at least 20, and every integer therebetween. The repeating units may include a number of contiguous repeating units, wherein the number is selected from the group consisting of: at least 3, at least 4, at least 5, at least 6, at least 7, at least 8, at least 9, at least 10, at least 15, at least 20, and every integer therebetween. In some embodiments the polymer may consist essentially of the repeating unit.

The repeating units of the polymer may include, for example, oligosaccharides, oligopeptides, oligonucleotides, analogs and combinations thereof, as described above. The repeating units may be composed of subunits, for example monosaccharides, amino acids, nucleotides, nucleosides, and analogs thereof, as described above. The immunomodulatory polymer can in some embodiments be a mixed polymer. A mixed polymer is a polymer that contains at least two different types of subunits, e.g., monosaccharides and amino acids.

As previously described, the positive charge of the charge motif is preferably a free amino group, and the negative charge of the charge motif is preferably carboxyl, phosphate, phosphonate, sulfate, or sulfonate. In a preferred embodiment the negative charge of the charge motif resides with a carboxyl group.

In certain embodiments the three-dimensional solution conformation comprises a helix. The helix may include an integer number or a non-integer number of repeating units per turn, and it may be a left-handed helix or a right-handed helix. In a preferred embodiment the helix has a pitch of about 20 Å.

In certain embodiments the immunomodulatory polymer may specifically exclude any of the following: PS A1, PS B, *Salmonella typhi* Vi antigen, *Escherichia coli* K5 antigen, *Staphylococcus aureus* type 5 capsular polysaccharide, *Rhizobium meliloti* exopolysaccharide II, group B streptococcus type III capsular polysaccharide, *Pseudomonas aeruginosa* Fisher immunotype 7O-antigen, *Shigella sonnei* Phase I lipopolysaccharide O-antigen, *Streptococcus pneumoniae* type I capsular polysaccharide, *Streptococcus pneumoniae* group antigen: C substance, or *Trypanosoma cruzi* lipopeptidophosphoglycan.

The polymers of the invention encompass many types of polymers. A "polymer" as used herein is a compound having a linear backbone of individual units which are linked together by linkages. The term "backbone" is given its usual meaning in the field of polymer chemistry. The polymers may be heterogeneous in backbone composition (referred to herein as a mixed polymer), so long as they have the requisite charge motif, thereby containing any possible combination of polymer units linked together such as peptide-nucleic acids (which have amino acids linked to nucleic acids). In some cases the polymers may differ from those polymers conventionally known in the art because the polymers of the invention may have non-polymeric compounds incorporated into the backbone. For instance, the polymer of the invention may be composed entirely of amino acids except for a region which contains an organic linker that links two sets of amino acids together. In a preferred embodiment the polymers are homogeneous in backbone composition and are, for example, polypeptides, polysaccharides, and carbohydrates. A "nucleic acid" as used herein is a biopolymer comprised of nucleotides, such as deoxyribonucleic acid (DNA) or ribonucleic acid (RNA). A polypeptide as used herein is a biopolymer comprised of linked amino acids. A polysaccharide as used herein is a biopolymer comprised of linked sugars.

The polymers may be composed of repeating units, for instance, the entire polymer may be composed of the repeating charge motif. A "unit" is used herein consistently with its known meaning in the art to indicate a building block of a polymer, e.g., a unit of a protein is an amino acid, a unit of a nucleic acid is a nucleotide, a unit of a polysaccharide is a monosaccharide, etc. A polymer composed of repeating units is one which is composed entirely of sets of units which occur at least two times within a polymer. The repeating units of the polymer may be identical or non-identical repeating units. An "identical repeating unit" as used herein is a set of units that is repeated within the polymer and in which all of the members have the identical composition and are positioned in the identical order to the members of the other sets of units. A "non-identical repeating unit" as used herein is a set of units that is repeated within the polymer and in which all of the members do not have the identical composition and/or are not positioned in the identical order to the members of the other sets of units. Some of the members of non-identical repeating unit may have the identical order and/or position as the members of the other sets as long as all the members are not identical. When used in the context of this invention a polymer having non-identical repeating units is a polymer which may have all non-identical repeating units or a combination of identical and non-identical repeating units.

The polymers of the invention may also be composed of non-repeating units. A polymer composed of non-repeating units, as used herein, is a polymer which is not entirely composed of repeating units. For instance, a polymer composed of non-repeating units may be a random polymer. A "random" polymer is a polymer having units which have no specific or identifiable order other than the repeating charge motif A polymer composed of non-repeating units also may be a hybrid repeat polymer which is partially random but which includes some repeating motifs.

The polymer includes at least two repeating charge motifs. A "repeating charge motif" as used herein is a motif composed of a positively charged free amino moiety and a negatively charged moiety. The motif may be composed of a dually charged single unit or of multiple units, one unit having the positive charge and a second unit having the negative charge. In the case that the charges are present on different units, the units may be adjacent to one another or may be separated by other charged or neutral units. Preferably the charged units are separated by neutral units. A neutral unit is a unit which does not have a positive and/or a negative charge. The charged units of the motif may be separated by any number but preferably by less than 10 neutral units. A repeating charge motif may be present in any orientation within the polymer. For instance, in a polymer having two repeating charge motifs separated by neutral units the polymer may have the following sequence: a positive charge first followed by a negative charge, followed by neutral units followed by a negative charge and finally a positive charge. Alternatively the polymer may have the following sequence: a positive charge first followed by a negative charge, followed by neutral units followed by a positive charge and finally a negative charge, etc.

A "negatively charged moiety" as used herein refers to any negatively charged group but is preferably a carboxyl group. Positively charged amino acids having a free amino group include but are not limited to lysine (K), arginine (R), asparagine (N), and histidine (H). Negatively charged amino acids include but are not limited to aspartic acid (D) and glutamic acid (E).

The immunomodulating polymer has a plurality of repeating charge motifs but may have any number greater than two. The whole polymer, for instance, may be composed of repeating charge motifs. Alternatively the polymer may be composed of any number of repeating charge motifs between two and the number when the entire polymer is composed of repeating charge motifs (which of course will depend on the size of the polymer). The polymer may have, for instance, at least 10, 15, 20, 25, 30, 35, etc., repeating charge motifs.

According to certain embodiments the charge motifs are separated from one another by less than a maximum distance. This maximum distance is quantitated as the distance between the positively charged free amino moieties of the at least two repeating charge motifs, as measured along the primary structure backbone when laid out in essentially linear fashion. Alternatively the distance could be similarly quantitated as the distance between the negatively charged moieties of the at least two repeating charge motifs. The distance, 32 Å, is equivalent to a distance of up to 8 amino acid residues of a polypeptide, measured in primary sequence. The distance between the motifs, of course, may be shorter when measured in the tertiary conformation, but for purposes of clarity is measured in terms of the primary structure. A polypeptide unit having this size is composed of a maximum size corresponding to 10 amino acid residues and having the following structure, wherein each X is the positively charged free amino moiety of the repeating charge motif; and each N is independently a neutral or charged unit which could include a repeating charge motif:

$XN_8X$

The negatively charged moiety of the repeating unit may be on either side of the X. The formula $XN_8X$ may be the entire polymer or may be a subset of a larger polymer.

The region between the repeating charge motif may be composed of repeating charge motifs, other units or subunits, or a mixture thereof. The region may be for instance an intervening sequence that is neutral. The intervening sequence may be the same type of unit as the other units of the polymer or may be completely different. For instance, it may be a non-polymeric organic moiety.

Both the positively and negatively charged groups on these polymers modulate their ability to influence the immune system and to protect animals against abscess formation. Total neutralization of either charge abrogates the immunomodulating ability of the polymers.

The immunomodulating polymers of the invention are polymers having the requisite charge motif described above and which have the ability to perform any of the functions such as induction of IL-2 and IL-10 secretion as described herein. In addition to the specific examples of preferred immunomodulating polymers of the invention provided herein, other preferred polymers can be identified and tested for their ability to induce secretion of IL-2 or IL-10 or to alter other immune function. Polymers can be identified, for instance, in a library of compounds or synthesized de novo. These compounds can then be tested for activity in any standard IL-2 or IL-10 induction assay. Such assays are well known to those of ordinary skill in the art. For instance the in vivo RNA analysis may be used or a protein analysis may be performed using anti-IL-2 or IL-10 antibodies. Additionally, in vitro assays using T cells may be used. The polymer can be added to a population of T cells in culture and production of IL-2 or IL-10 can be assessed.

The immunomodulating polymer of the invention may be derived from any source, e.g., they may be isolated and derived from natural sources such as animal or plant extracts, bacteria, fungi, seaweed and the like or synthetically prepared. For instance, when the polymer is a polypeptide it may be synthesized using conventional methods known in the art for synthesizing polypeptides. For instance, random polypeptides may be prepared according to the process disclosed in U.S. Pat. No. 3,849,550 and in Teitelbaum et al., *Eur J Immunol* 1:242 (1971). These references describe preparation of amino acids, wherein the N-carboxyanhydrides of tyrosine, alanine, gamma-benzyl glutamate and epsilon-N-trifluoroacetyllysine are polymerised at ambient temperature in indioxane with diethylamine as initiator followed by deblocking of the gamma-carboxyl group of the glutamic acid with hydrogen bromide in glacial acetic acid and removal of the trifluoroacetyl groups from the lysine residues by 1M piperidine. Polypeptides having specific sequences and other amino acids may also be prepared using equipment and methodology that is well known in the art.

Alternatively, polypeptides may be prepared using recombinant technology. Such methods are well known in the art and have been described in many references. See, e.g., Sambrook et al., *Molecular Cloning: A Laboratory Manual*, Second Edition, Cold Spring Harbor Laboratory Press, 1989.

Additionally, the polymers may be prepared from existing (or synthetic) polymers using chemical modification of neutral units to develop the positive and negative charges. For instance, the polymers may be chemically modified according to the process disclosed in U.S. Pat. Nos. 5,700,787 and 5,679,654 for modifying polysaccharides. Briefly, the N-acetyl moiety of native polysaccharide units can be modified to yield a free amino group. Thus a polysaccharide composed of units having a negative charge and a N-acetyl group, such as *Staphylococcus aureus* type 5 capsular polysaccharide, can be modified such that each monomeric repeating unit then has both a positively and negatively charged group. For those polysaccharides that contain imine moieties (C=NH), free amino groups also can be formed by conventional chemistry techniques known to those of ordinary skill in the art. One suitable method involves the use of sodium borohydride. The imine group can be reduced with sodium borohydride to create a free amino group. This is done by adding in excess of 5 mg of borohydride to polysaccharide dissolved in distilled water while stiring at room temperature for 2 hours. The mixture is then dialyzed against water and freeze dried.

The polymer also may be chemically modified according to procedures described in Wold, F., Posttranslational protein modifications: Perspectives and prospectives, in B. C. Johnson (Ed.), *Posttranslational Covalent Modification of Proteins*, New York; Academic, 1983, pp. 1-12, for modifying polypeptides and amino acids.

Polymers useful according to the invention also may be obtained from commercial sources.

A "synthetic polymer" as used herein is a polymer which is prepared by chemical or recombinant techniques and not otherwise found in nature. Synthetic polymers may be but are not necessarily identical in sequence to a naturally occurring polymer. Examples of and methods for preparing synthetic polymers are well known by those of ordinary skill in the art, including polysaccharides, polypeptides, polynucleotides, peptide nucleic acids, etc.

Synthetic polymers may also include polymers resembling naturally occurring polymers but having a modified backbone. Examples of such polymers with modified backbones are well known by those of ordinary skill in the art, and include for example, without limitation, phosphorothioate nucleic acids, methylphosphonate nucleic acids, and peptide nucleic acids.

A "non-native polymer" as used herein is a polymer that differs in composition or sequence from native naturally occurring polymers. It could not be prepared solely by isolation from natural sources without further modification.

The charge ratio of the polymer will depend on the number of positive and negative charges within the polymer and will vary depending on the polymer. In some instances when the polymer is a polypeptide it has a positive-to-negative charge ratio of 1:1.

The size of the polymers useful according to the invention varies greatly. Polymers between 0.5 kDa and 50 kDa will be typical, particularly for non-polysaccharide polymers. In one embodiment the polymer size is between 7 kDa and 25 kDa. In some embodiments the polymer size is between about 50 kDa and less than about 500 kDa. In yet other embodiments the polymer size is between about 500 kDa and about 5000 kDa.

The immunomodulating polymers of the invention are useful for a variety of in vitro and therapeutic purposes including but not limited to treating interleukin 2 (IL-2)-responsive disorders, protecting animals against abscess formation, preventing adhesion formation, e.g., reducing postoperative surgical adhesion formation, treating Th1-responsive disorders, treating autoimmune disease, and promoting allograft survival.

Thus the invention in one aspect is a method for inducing IL-2 secretion. This method can be performed by contacting an IL-2 secreting cell with an effective amount for inducing IL-2 secretion of a polymer of the invention. IL-2 is a cytokine which is well known to those of ordinary skill in the art and exerts a variety of effects. Among the physiological effects of IL-2 are induction of proliferation and activation of immune cells, particularly T lymphocytes, NK cells, and B lymphocytes. For a review, see Paul W E (1999) *Fundamental Immunology*, 4th ed., Lippincott-Raven, Philadelphia.

An IL-2 secreting cell is any cell which produces IL-2 in response to activation with the non-polysaccharide polymer of the invention. These cells include, for instance, T lymphocytes, including CD4+Th1 and CD4+Th2 cells and CTL's (CD8+). The IL-2 secreting cell is contacted with an effective amount of the polymer for inducing IL-2 secretion. An effective amount for inducing IL-2 secretion is that amount which results in any induction in IL-2 secretion. If the IL-2 secreting cell, for instance, is not secreting any IL-2 at the time that it is contacted with the polymer, then the ability of the polymer to induce any IL-2 is an effective amount of the polymer. If the IL-2 secreting cell is already producing IL-2, then the ability of the polymer to increase that amount is also an effective amount of the polymer.

There are many instances in which it is desirable to induce IL-2. It is desirable to induce IL-2, for instance, in vitro for a variety for experimental assays. An example of such an assay is an assay for identifying compounds useful for blocking IL-2 induction. Other assays include physiological assays for determining the effects of IL-2 on various systems. It is also desirable to induce IL-2 in a variety of ex vivo/in vivo conditions. It is known, for instance, that IL-2 is useful in the treatment of HIV infection, acquired immunodeficiency syndrome (AIDS), and cancer, e.g., renal cell carcinoma, and melanoma.

Thus the invention also encompasses a method for treating an IL-2-responsive disorder by inducing IL-2 secretion. A subject having an IL-2-responsive disorder is administered an effective amount for inducing IL-2 secretion of an immunomodulating polymer of the invention. The subject having an IL-2-responsive disorder is one who is not preparing to undergo surgery. Generally, the subject is one who has or is at risk of developing AIDS or cancer, e.g., renal cell carcinoma or melanoma.

Numerous conditions, particularly those involving T-cell dependent immune response, may benefit from the use of the methods and compositions disclosed herein. For example, subjects that are immunodeficient due to a limited ability to mount an effective T-cell response, for instance those infected with human immunodeficiency virus (HIV), are known to benefit from increased levels of IL-2.

The invention is also useful whenever it is desired to induce secretion of IL-10. It is now believed that IL-10 plays an important role in numerous immune-mediated conditions, including inflammatory conditions. Without meaning to be bound to any particular theory or mechanism, it is believed that the polymers of the invention not only induce the secretion of IL-2, as an initial step, but also subsequently induce the secretion of IL-10. Thus, it is believed that the secretion of IL-10, which is observed following administration of the polymers of the invention, is indirect, i.e., mediated by effects arising as a result of the IL-2 secretion. IL-10 is a cytokine which is well known to those of ordinary skill in the art and exerts a variety of physiologic effects. It is considered to be a key Th2 cytokine which is known to inhibit Th1 function, including production of IL-2. IL-10 has been shown by others to prevent many types of inflammatory processes such as sepsis, inflammatory bowel diseases, and adhesions. In addition, IL-10 prevents certain autoimmune diseases, graft-versus-host disease (GvHD), and psoriasis. Thus, the polymers of the invention are useful for treating or preventing, for example, disorders such as, sepsis, inflammatory bowel disease, pelvic inflammatory disease (PID), urinary tract infections, cancer, or adhesions.

The instant invention is also useful whenever it is desirable to prevent bacterial abscess formation in a subject. This includes prophylactic treatment to prevent such conditions in planned surgical procedures as well as emergency situation. Elective surgeries include the following intraabdominal surgeries: right hemicolectomy, left hemicolectomy; sigmoid colectomy; subtotal colectomy; total colectomy; laparoscopic or open cholecystectomy; gastrectomy, etc. Emergency intraabdominal surgeries include those to correct the following conditions: perforated ulcer (duodenal or gastric); perforated diverticulitis; obstructive diverticulitis; acute appendicitis; perforated appendicitis; blunt abdominal trauma; penetrating abdominal trauma; second operation to drain abscess; etc. The invention also is useful with nonintraabdominal surgeries such as cardiac surgeries and surgeries to correct wound infections. The invention also is useful in connection with diseases that predispose a subject to abscess formation such as pelvic inflammatory disease (PID), urinary tract infections and colon cancer. Those of ordinary skill in the art to which this invention pertains will recognize the range of conditions and procedures with which the invention is useful.

When administered to prevent abscess formation, the immunomodulating polymers of the invention may be administered with an adjuvant. The term "adjuvant" includes any substance which is incorporated into or administered simultaneously with the polymer and which potentiates the immune response in the subject. Adjuvants include aluminum compounds, e.g., gels, aluminum hydroxide and aluminum phosphate, and Freund's complete or incomplete adjuvant (in which the polymer is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium bovis*), calcium phosphate, levamisole, isoprinosine, polyanions (e.g., poly A:U), lentinan, pertussis toxin, lipid A, saponins, peptides (e.g., muramyl dipeptide) and rare earth salts (e.g., lanthanum and cerium). The amount of adjuvant depends on the subject and the particular polymer used and can be readily determined by one skilled in the art without undue experimentation. Preferred adjuvants are those that selectively stimulate T cells. It is desirable to avoid adjuvants that might suppress a T cell response.

The instant invention is also useful whenever it is desirable to prevent adhesion formation, e.g., postoperative surgical adhesion formation, in a subject. In another aspect of the invention, a method is provided for inducing protection against postoperative surgical adhesion formation associated with many common types of surgery. This includes prophylactic treatment to prevent adhesion formation following planned surgical procedures as well as following emergency operations. It was discovered that administration of the polymer at a site separate from the operative site is capable of inducing protection against postoperative surgical adhesion formation.

The invention also is useful in connection with diseases that predispose a subject to spontaneous adhesion formation such as pelvic inflammatory disease, inflammatory bowel disease, urinary tract infections and colon cancer. The invention thus is useful with inflammatory processes involving virtually any tissue or organ. Those of ordinary skill in the art to which this invention pertains will recognize the range of conditions and procedures with which the invention is useful.

When administered to prevent postoperative surgical adhesion formation, the polymers of the invention may be administered either distant from the operative site, including systemically, or locally into the operative site at which it is desirable to reduce the likelihood of postoperative surgical adhesion formation. The polymers of the invention can be administered as aqueous solutions, as crosslinked gels, or as any temporal or physical combination of aqueous solution and crosslinked gel forms. Crosslinked gels must retain the repeating charge motif, namely, the positively charged free amino moiety and a negatively charged moiety, to an extent sufficient for the purpose of reducing or preventing postoperative surgical adhesion formation according to the invention.

It has been discovered that certain polymers can be used to stimulate host T cells and induce protection against numerous bacteria. This protective effect is T-cell-dependent and not mediated by a humoral antibody response. As such, administration of the preparations of the invention is not "vaccination" and the preparations are not "vaccines" which mediate protection that is specific to bacteria expressing the immunizing antigen.

It was also found according to the invention that the immunomodulating polymers described above are useful for activating T cells to produce Th1 cytokines. The instant invention is useful whenever it is desired to stimulate T cells in a treated host subject. In particular, the invention is useful whenever it is desired to induce protection of the treated host against infection by any of a number of different bacteria This protective effect is T-cell dependent and not necessarily mediated by a humoral antibody response.

The T cell is contacted with an effective amount for inducing IL-2 secretion of the immunomodulating polymer of the invention. The immunomodulating polymer activates T cells causing secretion of Th1 specific cytokines, such as IL-2 and interferon-γ (IFN-γ). When T cells are stimulated, they can differentiate toward either Th1 or Th2 cytokine production. The immunomodulating polymers of the invention can activate T cells to mediate cytokine release having a profile of Th1 cytokines and thus are useful any time it is desirable to activate T cells to produce a Th1 cytokine profile.

A "T cell" as used herein is a thymus-derived lymphocyte characterized in part by the expression on its cell surface of CD3 and a T cell antigen receptor. A "Th1 cell" as used herein is a CD4+T lymphocyte that secretes principally IL-2, IFN-γ, and lymphotoxin. A Th1 cytokine profile includes IL-2, IFN-γ, and lymphotoxin.

The invention also encompasses methods for treating a Th1-cell-responsive disorder by activating a T cell to produce Th1-cell-specific cytokines. The method is accomplished by administering to a subject having a Th1-cell-responsive disorder an effective amount for inducing IL-2 secretion by the T cell an immunomodulating polymer of the invention. A subject having a Th1-cell-responsive disorder is a subject who is not preparing to undergo surgery but who is at risk of developing or has a Th1-cell-responsive disorder. A "Th1-cell-responsive disorder" is an immune-mediated disorder which is inhibited with Th1 cytokines. A disorder is inhibited as used herein if the development of disorder is partially or completely prevented or if the magnitude of the disorder is reduced. Th1-cell-responsive disorders include but are not limited to insulin-dependent diabetes mellitus, experimental allergic encephalomyelitis, inflammatory bowel disease, and allograft rejection.

It was also discovered according to the invention that certain immunomodulating polymers of the invention are useful for suppressing IgG antibody response to specific antigen and also to promote allograft survival. The immunomodulating polymers useful according to these aspects of the invention include the polymers discussed above except for those which are composed of alanine, glutamic acid, lysine, and tyrosine in a molar ratio of approximately 6:2:5:1 or in a ratio of 4-6:1.4-2.1:3.2-4.2:1, 6:2:4.5:1, 4.1-5.8:1.4-1.8:3.2-4.2:1, 6:1.9:4.7:1, 4.9:1.7:3.8:1, or 6:1.8:4:1. In general the polymer, when composed only of glutamic acid, lysine, alanine, and tyrosine specifically excludes those forms of GLAT and copolymer 1 described in the literature. In some embodiments the immunomodulating polymers of the invention are useful for treating these disorders in a subject that is not preparing to undergo surgery.

A "disorder characterized by an inappropriate IgG antibody response to specific antigen" as used herein is a disorder such as acute glomerulonephritis, Goodpasture's syndrome, certain autoimmune arthritidies including rheumatoid arthritis, systemic lupus erythematosus (lupus), AIDS, Sjögren's syndrome, autoimmune hemolytic anemia, idiopathic thrombocytopenic purpura (ITP), and certain forms of thyroiditis.

The polymers are also useful for promoting allograft survival. The term "promoting allograft survival" as used herein denotes the clinically measurable extension or preservation of physiologically useful function of transplanted cells, tissues, or organs derived from another individual of the same species as the recipient, beyond the corresponding function of similar transplants in untreated recipients.

The polymers of the present invention have adjuvant properties by themselves. To the extent that the polymers described herein potentiate human immune responses, they can be used as adjuvants in combination with other materials.

The present invention provides pharmaceutical compositions, for medical use, which comprise polymers of the invention together with one or more pharmaceutically acceptable carriers and optionally other therapeutic ingredients. Thus the invention also relates to pharmaceutical compositions of the above described immunomodulating polymers in combination with an adjuvant or an antibacterial agent or other therapeutic agent and a pharmaceutically acceptable carrier.

The polymers useful in the invention may be delivered separately with another anti-bacterial antibiotic drug or in the form of anti-bacterial, antibiotic cocktails. An anti-bacterial antibiotic cocktail is a mixture of any polymer useful with this invention and an anti-bacterial antibiotic drug and/or supplementary potentiating agent. The use of antibiotics in the treatment of bacterial infection is routine. In this embodiment, a common administration vehicle (e.g., tablet, implant, injectable solution, etc.) could contain both the polymer and the anti-bacterial antibiotic drug and/or supplementary potentiating agent. Alternatively, the anti-bacterial antibiotic drug can be separately dosed. Anti-bacterial antibiotic drugs are well known and include, without limitation: amdinocillin, aminoglycosides, amoxicillin, ampicillin, avlocillin, bacampicillin, carbenicillin, cefaclor, cefadoxil, cefamandole, cefazolin, cefinenoxine, cefonicid, cefoperazone, cefotaxime, cefotetan, cefoxitin, ceftazidme, ceftizoxime, ceftriaxone, cefuroxime axetil, cephalexin, cephradine, chloramphenicol, clavulanate, clindamycin, cloxacillin, cyclacillin, dicloxaciffin, epicillin, erythromycin, flucloxacillin, hetacillin, imipenem, lincomycin, methicillin, metronidazole, mezlociliin, moxalactam, nafcillin, neomycin, oxacillin, penicillin G, penicillin V, piperacillin, pivampicillin, quinolones, rifampin, sulbactam, tetracyclines, ticarcillin, timentin, trimethoprim-sulfamethoxazole, and vancomycin. (See Goodman and Gilman's *Pharmacological Basis of Therapeutics,* 8th ed., 1993, McGraw Hill, Inc.) The precise amounts of the therapeutic agent used in combination with the polymers of the invention will depend upon a variety of factors, including the polymer selected, the dose and dose timing selected, the mode of administration, the nature of any surgery contemplated and certain characteristics of the subject. Where local administration is carried out, it will be understood that very small amounts may be required (nanograms and possibly picograms). The precise amounts selected can be determined without undue experimentation, particularly since a threshold amount will be any amount which will favorably enhance the immune response. Thus, it is believed that picogram to milligram amounts are possible, depending upon the mode of delivery, but that nanogram to microgram amounts are likely to be most useful.

The compounds are administered in an effective amount for producing the desired biological result. It is believed that doses ranging from 1 nanogram/kilogram to 100 milligrams/ kilogram, depending upon the mode of administration, will be effective. The preferred range is believed to be between 500 nanograms and 500 micrograms/kilogram, and most preferably between 1 microgram and 100 micrograms/kilogram. The absolute amount will depend upon a variety of factors (including whether the administration is in conjunction with elective surgery or emergency surgery, concurrent treatment, number of doses and individual patient parameters including age, physical condition, size and weight) and can be determined with no more than routine experimentation. It is preferred generally that a maximum dose be used, that is, the highest safe dose according to sound medical judgment.

In one embodiment an effective amount is that amount for producing a biological result inducing protection against abscess formation. An effective amount for inducing protection against abscess formation as used herein is that amount of an immunomodulating polymer of the invention that will, alone or together with further doses or additional therapeutic compounds, inhibit or prevent the formation of abscess resulting from infection by particular bacteria.

Multiple doses of the pharmaceutical compositions of the invention are contemplated, particularly when administered in conjunction with a surgical procedure. Multiple doses may be administered over a three week period preceding surgery, over a two week period preceding surgery, over a one week period preceding surgery, or 24 hours preceding surgery. Additionally one or more doses may be administered after exposure to bacteria or after surgery. Any regimen that results in an enhanced immune response to bacterial infection/contamination and subsequent abscess formation may be used, although optimal doses and dosing regimens are those which would not only inhibit the development of abscess formation, but also would result in a complete protection against abscess formation by a particular bacterial organism or a variety of bacterial organisms. Desired time intervals for delivery of multiple doses of a particular polymer can be determined by one of ordinary skill in the art employing no more than routine experimentation.

Another desired biological result is prevention of adhesion formation. Thus, the compounds may be administered in an effective amount for inducing protection against adhesion formation. An effective amount for inducing protection against postoperative surgical adhesion formation as used herein is that amount of an immunomodulating polymer of the invention that will, alone or together with further doses or additional therapeutic compounds, inhibit or prevent the formation of postoperative surgical adhesion.

The preparations of the invention when administered for the purpose of preventing abscess formation may be administered "in conjunction with" infection, meaning close enough in time with the surgery, trauma or diseases that predispose the host to abscess formation so that a protective effect against abscess formation is obtained. The preparations may be administered long before surgery in the case of elective surgery (i.e., weeks or even months) preferably with booster administrations closer in time to (and even after) the surgery. Particularly in emergency situations, the preparations may be administered immediately before (minutes to hours) and/or after the trauma or surgery. It is important only that the preparation be administered close enough in time to the surgery so as to enhance the subject's immune response against bacterial infection/contamination, thereby increasing the chances of a successful host response and reducing the likelihood of abscess formation.

The invention relates in part to pharmaceutical compositions of immunomodulating polymers and methods of use thereof. Thus in one aspect the invention is a pharmaceutical composition for activating immune cells that includes an effective amount, for activating immune cells, of an immunomodulatory polymer as described above, and a pharmaceutically acceptable carrier. In a preferred embodiment the immunomodulatory polymer of the pharmaceutical composition according to this aspect of the invention is PS A2, or functional equivalents thereof.

Thus, the formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The polymer may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a polymer optionally included in a pharmaceutically acceptable carrier. The term "pharmaceutically acceptable carrier" means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the polymers of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The polymers useful in the invention may be delivered in mixtures of more than one polymer. A mixture may consist of several polymers.

A variety of administration routes are available. The particular mode selected will depend, of course, upon the particular polymer selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous, intravenous, intramuscular, or intraperitoneal injection or infusion techniques.

The compositions may conveniently be presented in unit dosage form and may be prepared by any of the methods well known in the art of pharmacy. All methods include the step of bringing the polymer into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In other aspects the invention provides a system and a method for selecting a candidate immunomodulatory polymer based on certain parameters related to the three-dimensional solution conformation of the candidate immunomodulatory polymer. Due to the complexity of the process of selecting even one candidate immunomodulatory polymer based on the above parameters, the system and method are preferably computer-implemented. The method involves predicting three-dimensional solution conformation of a polymer based on primary structure of a candidate immunomodulatory polymer and selecting the candidate immunomodulatory polymer if its predicted three-dimensional solution conformation includes a plurality of repeating units, a plurality of solvent-accessible charges, and a plurality of docking sites, each docking site being about 10 Å wide and about 5 Å deep.

Computer-based methods of predicting and analyzing three-dimensional solution phase conformation of macromolecules are well known by those of ordinary skill in the art. Examples include PCT publication WO 98/47089 by Mayo et al.; U.S. Pat. No. 6,110,672 to Mandel et al.; U.S. Pat. No. 5,888,741 to Hendry; U.S. Pat. No. 5,331,573 to Balaji et al.; Dahiyat B I et al. (1997) *Science* 278:82-7; and Schneider G et al. (2000) *J Comput Aided Mol Des* 14:487-94. In addition, there are a number of computer software applications and packages commercially available for this purpose, including, for example, Insight II 98.0 from Molecular Simulations, San Diego, Calif., for visualization, modeling, forcefield calculations, energy minimizations, and molecular dynamics simulations. Computer hardware suitable for running such programs are commercially available, including, for example, Orion 200 workstation equipped with two R12000 270 MHz and two R10000 180 MHz IP27 central processing units (CPUs; Silicon Graphics, Mountain View, Calif.). So-called neural networks may be used to particular advantage in performing the types of simulations and calculations involved in predicting and analyzing three-dimensional solution phase conformation of macromolecules. See, for example, Baldi P (1999) *Bioinformatics* 15:937-46; Stahl M et al. (2000) *Protein Eng* 13:83-8.

Computer input data for carrying out the calculations includes at least enough information to specify the chemical identity, as a structural formula, of the candidate immunomodulatory polymer, i.e., the chemical relationships (covalent bonds) among all the atoms of the molecule. In some instances it may be sufficient to infer the existence and nature of certain bonds, as for example input data based on low-resolution crystal structure. The input data may be derived from any of a number of possible physical and chemical sources, including chemical analysis, physical analysis (e.g., melting point, freezing point depression, etc.), sequencing analysis, NMR data, crystal structure data, mass spectroscopy, gas chromatography, optical analysis including circular dichroism data, as well as other methods well known by those of ordinary skill in the art.

The computer input data may specify an entire polymer, part of a polymer, or only a unit of a polymer as defined above. In the instance where the input data includes data only specifying a unit of a polymer, the computer can use the data to build up a structure having a plurality of units so provided.

In certain preferred embodiments the computer input data includes a library of candidate immunomodulatory polymers. The library includes a plurality of candidate immunomodulatory polymers, of varying degrees of chemical relatedness and unrelatedness, and may include as few as two and as many as tens, hundreds, thousands, or even more candidate immunomodulatory polymers. The library may include data specifying entire polymers, parts of polymers, or only units of polymers as defined above.

The software operated by the computer calculates for each candidate immunomodulatory polymer a three-dimensional solution phase conformation for that polymer. Such calculations include many parameters related to size, charge, distance, and energy, and typically involve energy minimization calculations designed to arrive at a conformation that is both chemically and physically reasonable.

After the three-dimensional solution phase conformation for a candidate immunomodulatory polymer has been predicted, the candidate polymer is either selected or not selected, based on the presence or absence of certain features. These features include, at a minimum, a plurality of repeating units, a plurality of solvent-accessible positive and/or negative charges, and a plurality of docking sites, each docking site being about 10 Å wide and about 5 Å deep. Additional features which may be considered in choosing to select a particular candidate polymer may include the presence of a repeating charge motif, where the repeating charge motif is a positive charge and a negative charge. In certain preferred embodiments the positive charge of a repeating charge motif in a selected candidate immunomodulatory polymer having the repeating charge motif is provided by a free amino group. In certain preferred embodiments the negative charge of a repeating charge motif in a selected candidate immunomodulatory polymer having the repeating charge motif is provided by a carboxyl, phosphate, phosphonate, sulfate, or sulfonate moiety.

Further additional features which may be considered in choosing to select a particular candidate polymer may include the relationship of the repeating units along the backbone. In certain embodiments the repeating units are contiguous. In some embodiments the repeating units may be separated by intervening sequence.

Yet further additional features which may be considered in choosing whether to select a particular candidate polymer may include the assumption by the polymer of a helix conformation. Either the entire polymer may be a helix, or part of the polymer may include a helix domain. The helix may be left-handed or right-handed. In some embodiments the helix has a pitch of about 20 Å. For example, PS'A2 has a right-handed helix with a pitch of 20 Å, and Sp1 has a right-handed helix with a pitch of 19 Å (see further below). In some embodiments the repeating units occur in integer multiples per turn of the helix. For example, PS A2 has two repeating units per turn of the helix. In some embodiments the repeating units may occur in non-integer multiples per turn of the helix.

Further characteristics of docking sites may be used as criteria for choosing to select a given candidate polymer. These characteristics include the length of the docking site and the affinity of the docking site for an alpha helix of a polypeptide. In preferred embodiments the length of the docking site is at least about 10 Å. Substantially shorter docking sites may limit specificity or affinity for potential docking partners. In certain embodiments the docking site of a selected candidate immunomodulatory polymer is constructed and arranged to bind, under physiologic conditions, an alpha helix of a polypeptide with an affinity of at least $10^{-3}$ $M^{-1}$, and more preferably with an affinity of at least $10^{-6} M^{-1}$, and even more preferably with an affinity of at least $10^{-9} M^{-1}$. The affinity may be determined by molecular modeling calculation or by empirical measurement. Methods for empirical measurement may be based on experiments involving affinity chromatography, surface plasmon resonance (SPR, BIA), circular dichroism, as well as other methods that will be apparent to those of ordinary skill in the art.

In certain embodiments the selected candidate immunomodulatory polymer has a sugar backbone. In some preferred embodiments the selected candidate immunomodulatory polymer is a polysaccharide. In some embodiments the selected candidate immunomodulatory polymer is a polypeptide.

In further aspects the invention provides a system and a method for designing a candidate immunomodulatory polymer based on knowledge of the three-dimensional solution structure of an immunomodulating polymer such as PS A2. The system and method thus may be used for rational drug design. Due to the complexity of the system and method, the system and method are preferably computer-implemented. Computer modeling is used to build up a polymer out of virtual subunits according to certain constraints imposed by a template three-dimensional structure, as well as to perform a comparison between a polymer so created in silico with the three-dimensional structure of the template provided by the reference immunomodulating polymer.

The method according to this aspect of the invention again uses a computer as previously defined, provided with a source of input data specifying the three-dimensional conformation of a template immunomodulatory polymer. Examples of computer programs that may be used to perform the method include Schneider G et al. (2000) *J Comp Aided Mol Des* 14:487-94 and PCT publication WO 98/47089 by Mayo et al.

The computer is also provided with a library of virtual subunits from which the program will select subunits to build up the polymer. Virtual subunits are defined above to correspond to computer-usable representations of real chemical entities such as sugars, amino acids, nucleotides, analogs thereof, as well as additional chemical moieties and substituents. The substituents may be viewed as side groups that can be added to or substituted for other substituents of a core structure, e.g., addition of a carboxyl group or an amino group to a monosaccharide.

The method as executed by the computer under the control of the program conforms to conventional rules of chemistry, e.g., rules of organic chemistry and biochemistry, in terms of chemical bond formation. Such rules are well known by those of ordinary skill in the art and may be found, for example in Morrison and Boyd, *Organic Chemistry* 3rd ed. (1973) Allyn and Bacon, Boston.

The systems and methods according to these aspects of the invention may further include empirical testing of a candidate immunomodulatory polymer. Such testing can be performed in vitro and in vivo, and includes contacting a candidate immunomodulatory polymer with an immune cell under conditions in which the immune cell is normally not activated, and measuring an activation marker of the contacted immune cell. Measurement of activation of an immune cell can be accomplished according to techniques including, for example, measurement of secreted products (e.g., cytokines, growth factors, chemokines, nitric oxide, antibodies), bioassay (e.g., cytotoxicity, granuloma formation, support of viability, etc.), surface marker analysis (FACS), calcium uptake or flux, respiratory activity, as well as other methods recognized by those of ordinary skill in the art. If the measurement shows that the immune cell is activated in association with contact with the candidate immunomodulatory polymer, the candidate immunomodulatory polymer is selected for further use or analysis. Conversely, if the measurement shows that the immune cell is not activated in association with contact with the candidate immunomodulatory polymer, the candidate immunomodulatory polymer is not selected for further use or analysis. A candidate immunomodulatory polymer according to this embodiment may be a previously selected candidate immunomodulatory polymer, based on the features described above (i.e., excluding the contacting and measuring), and then be further selected or not selected based on the results from the contacting and measuring. Alternatively, the initial selecting may occur upon inclusion of the contacting and measuring.

The methods, acts, systems, and system elements described above in relation to selecting or designing a candidate immunomodulatory polymer may be implemented using a computer system, such as the various embodiments of computer systems described below, although the methods, acts, systems, and system elements described above are not limited in their implementation to any specific computer system described herein, as many other different machines may be used.

Such a computer system may include several known components and circuitry, including a processing unit (i.e., processor), a memory system, input and output devices and interfaces, transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network.

The computer system may include a processor, for example, a commercially available processor such as one of the series x86, Celeron and Pentium processors, available from Intel, similar devices from AMD and Cyrix, the 680X0 series microprocessors available from Motorola, and the PowerPC microprocessor from IBM. Many other processors are available. The computer system is not limited to a particular processor.

A processor typically executes a program called an operating system, of which WindowsNT, Windows95 or 98, UNIX, Linux, DOS, VMS, MacOS and OS8 are examples, which controls the execution of other computer programs and provides scheduling, debugging, input/output control, accounting, compilation, storage assignment, data management and memory management, and communication control and related services. The processor and operating system together define a computer platform for which application programs in high-level programming languages are written. The computer system is not limited to a particular computer platform.

The computer system may include a memory system, which typically includes a computer readable and writeable non-volatile recording medium, of which a magnetic disk, optical disk, a flash memory and tape are examples. Such a recording medium may be removable such as, for example, a floppy disk, read/write CD or memory stick, or permanent, for example, a hard drive. Such a recording medium stores signals, typically in binary form (i.e., a form interpreted as a sequence of one and zeros). A disk (magnetic or optical) has a number of tracks on which such signals may be stored. Such signals may define a program, e.g., an application program, to be executed by the microprocessor, or information to be processed by the application program.

The memory system of the computer system also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium, e.g., disk.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer system that implements the methods, acts, systems and system elements described above in relation to selecting or designing a candidate immunomodulatory polymer is not limited to any particular mechanism. The computer system is not limited to a particular memory system.

At least part of such a memory system described above may be used to store one or more of the data structures described above in relation to the disclosed systems and methods for selecting or designing a candidate immunomodulatory polymer. For example, at least part of the non-volatile recording medium may store at least part of a database that includes one or more of such data structures. Such a database may be any of a variety of types of databases, for example, a flat-file database where data is organized into data units separated by delimiters, a relational database where data is organized into data units stored in tables, an object-oriented database where data is organized into data units stored as objects, or another type of databases.

The computer system may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer system may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer system also may include one or more input devices. Example input devices include a keyboard, keypad, track ball, mouse, pen and tablet, communication devices such as described above, and data input devices such as audio and video capture devices and sensors. The computer system is not limited to the particular input or output devices described herein.

The computer system may include specially programmed, special purpose hardware, for example, an application-specific integrated circuit (ASIC). Such special-purpose hardware may be configured to implement one or more of the methods, acts and systems described above in relation to the systems and methods disclosed herein for selecting or designing a candidate immunomodulatory polymer.

The computer system and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, acts and systems described above in relation to the systems and methods disclosed herein for selecting or designing a candidate immunomodulatory polymer may be implemented using any of a variety of suitable programming languages, including procedural programming languages, object-oriented programming languages, other languages and combinations thereof, which may be executed by such a computer system. Such methods and acts may be implemented as separate modules of a computer program, or may be implemented individually as separate computer programs. Such modules and programs may be executed on separate computers.

The methods, acts, systems, and system elements described above in relation to the systems and methods disclosed herein for selecting or designing a candidate immunomodulatory polymer may be implemented in software, hardware or firmware, or any combination of the three, as part of the computer system described above or as an independent component.

Such methods, acts, systems and system elements, either individually or in combination, may be implemented as a computer program product tangibly embodied as computer-readable signals on a computer-readable medium, for example, a non-volatile recording medium, an integrated circuit memory element, or a combination thereof. For each such method and act, such a computer program product may comprise computer-readable signals tangibly embodied on the computer-readable that define instructions, for example, as

EXAMPLES

Example 1

PS A2

Bacterial strain and isolation of capsular polysaccharides of *B. fragilis* strain 638R. *B. fragilis* strain 638R (Privitera G et al. (1979) *J Infect Dis* 139:97-101) was maintained in peptone-yeast broth at –80° C. The production of CPC was enhanced and the glycogen content in extracts was minimized by serial passage of bacteria five times through rat spleens (male Wistar rats, 175-200 g, Charles River Laboratories, Wilmington, Mass.). Kasper D L et al. (1980) *J Infect Dis* 142:750-6. Initially, $10^8$ organisms in PBS were injected intraperitoneally into a rat and recovered 24 h later by dispersing the spleen. The organisms were cultured overnight anaerobically on Brucella agar with 5% sheep blood (PML Microbiologicals, Mississauga, ON, Canada). The inoculation and recovery processes were repeated. Enhanced production of capsule was confirmed by electron microscopy studies with polyvalent antiserum to whole bacteria. After the passages, bacteria were grown anaerobically in a 16-liter batch culture as described previously. Pantosti A et al. (1991) *Infect Immunol* 59:2075-82; Tzianabos A O et al. (1992) *J Biol Chem* 267:18230-5. The cells were harvested by centrifugation (average wet weight, 244 g) and suspended in water. CPC was extracted from the bacterial cells with hot phenol/water and digested extensively with RNAse, DNAse, and pronase. The dialzyed product (average dry weight, 2 g) was chromatographed on a column of Sephracyl S-400 HR (Amersham Pharmacia Biotech, Piscataway, N.J.) in a 3% deoxycholate acid-containing buffer at pH 9.8 to separate lipopolysaccharide from CPC. Pantosti A et al. (1991) *Infect Immunol* 59:2075-82; Tzianabos A O et al. (1992) *J Biol Chem* 267:18230-5. Chromatographic fractions were analyzed throughout the isolation procedure by measurements of UV absorbance at 280, 260 and 206 nm, refractive index, and protein by the BCA method (Pierce, Rockford, Ill.), and by silver-stain SDS-PAGE gels (Laemmli UK (1970) *Nature* 227:680-5), dot blot, immunoelectrophoresis (IEP), and immunodiffsuion (Ouchterlony O (1958) *Prog Allergy* 5:1-78; Pantosti A et al. (1991) *Infect Immunol* 59:2075-82). After gel-filtration chromatography with S-400 HR, silver-stain SDS-PAGE showed fractions with a high-molecular-mass antigen ($\geqq$160 kDa according to protein standards) representing CPC. Subsequently eluted fractions showed antigen smaller than 20 kDa at the gel front that represented lipopolysaccharide (LPS) and digested protein and nucleic acid. Fractions eluted between CPC and LPS contained both materials. Fractions containing capsular polysaccharide exclusively and reacting with antiserum to the whole bacteria by double immunodiffusion were pooled, concentrated, alcohol precipitated, dialyzed and lyophilized. The CPC (average dry weight, 0.2 g) was examined by IEP (in 50 mM Tris buffer at pH 7.3), which showed three dominant components, two positively and one negatively charged, and two weak, distinct components migrating towards the anode and cathode.

Acid-treated (5% acetic acid at 100° C. for 1 h), dialyzed, and lyophilized CPC was loaded onto a column containing Q-Sepharose FF (Amersham Pharmacia Biotech) in 50 mM Tris buffer at pH 7.3. Antigens were eluted with Tris buffer and an NaCl gradient. Further purification steps required anion-exchange chromatography with S-Sepharose (Amersham Pharmacia Biotech) in water at pH 4, Q-Sepharose FF (Amersham Pharmacia Biotech) in 50 mM Tris buffer at pH 8.6, gel-filtration chromatography with Sephracyl S-300 HR (Amersham Pharmacia Biotech) in 50 mM PBS at pH 7.3, and isoelectric focusing. Separated polymers maintained their reactivity with the polyclonal antiserum. Fractions that appeared identical by the different measurements were pooled, dialyzed, lyophilized, and analyzed by high-resolution (500 MHz) proton nuclear magnetic resonance (NMR) spectroscopy. The final product was found to be essentially free of contaminating protein, nucleic acid, lipopolysaccharide, and lipids. Tzianabos A O et al. (1993) *Science* 262:416-9. The capsular polysaccharides were prepared in sterile, pyrogen-free saline for administration to animals.

PS A2 is encoded by a biosynthesis region in the same area of the 638R chromosome that encodes PS A1 of strain NCTC 9343. Comstock L E et al. (2000) (1999) *J Bacteriol* 181:6192-6. PS A2 showed a predominant neutral to positive charge motif at neutral pH that was unchanged at pH 6.2 and slightly shifted toward the anode at pH 8.6. Efforts to determine the exact isoelectric point of PS A2 by isoelectric focusing showed a wide distribution over a pH range between 4.5 and 10. However, structure and conformation of PS A2, as determined by a combination of various analyses, showed a polymer with one free amino group and one carboxyl group per repeating unit, properties that give the polymer an average net neutral charge motif and classify it as a balanced zwitterionic polysaccharide.

Animal model for abscess induction. In two independent experiments, 0.5 ml of injection volume containing 100, 10, 1, or 0.1 µg of capsular polysaccharide and sterile cecal contents (dilution, 1:4 in PBS) was administered intraperitoneally by injection through a 18-gauge needle to groups of six outbred male Wistar rats (150-175 g, Charles River Laboratories). As the control, PBS was substituted for the capsular polysaccharide. Six days after challenge, the rats were sacrificed and then examined for macroscopically visible intraperitoneal abscesses by observers unaware of treatment status. Grossly visible abscesses were confirmed microscopically. The development of one or more abscesses was considered a positive result.

Statistical analysis. In vivo experiments were analyzed in a structured logistic regression model that permitted evaluation of separate dose-response relationships (dose in micrograms) and direct interference on median abscess-induction dose, which is the theoretical dose of polysaccharide required to induce abscesses in 50% of animals ($AD^{50}$). Cox C (1990) *Biometrics* 46:709-18; Kalka-Moll W M et al. (2000) *J Immunol* 164:719-24; Tzianabos A O et al. (1993) *Science* 262:416-9. Likelihood-ratio tests were performed for hypotheses concerning commonality of dose-response slopes and $AD^{50}$s. Rats that died within 2 days after challenge were not included in the analysis because their deaths were due to anesthesia.

Biological activity of polysaccharides in experimental abscess formation. All the polysaccharides in the tested dose ranges induced intraabdominal abscesses in a dose-dependent fashion (PS A1 and PS A2, p<0.001). PS A1 of *B. fragilis* NCTC 9343 was the most potent abscess-inducing zwitterionic polysaccharide, with an $AD^{50}$ of 0.28 µg. The $AD^{50}$ of the zwitterionic polysaccharide PS A2 of strain 638R was 4.79 µg—17 times higher.

Compositional Analysis. The monosaccharide components of PS A2 were identified by gas chromatography-mass spectroscopy (GC-MS) analysis of the corresponding alditol acetate derivatives. Wang Y et al. (1994) *Carbohydr Res* 260:305-17. The D/L configurations of the sugar components were established by butanolysis, peracetylation, and GC-MS analysis. Gerwig G J et al. (1978) *Carbohydr Res* 62:349-57. Commercially available D- and L-fucose (Fuc), D-glycero-D-mannoheptose (Hep), and N-acetyl-D-mannosamine (ManNAc) served as standards (Fluka, Milwaukee, Wis.). PS A1 from *B. fragilis* 9343, which contains 2-acetamido-4-amino-2,4,6-trideoxygalactose, was also used as a standard. Pantosti A et al. (1991) *Infect Immun* 59:2075-82; Baumann H et al.(1992) *Biochemistry* 31:4081-9. Since no authentic standard for 3-acetamido-3,6-dideoxyglucose (ADG) was available, its configuration was derived from molecular modeling. Baumann H et al. (1992) *Biochemistry* 31:4081-9; Bock K (1983) *Pure Appl Chem* 55:605-22. The chirality of 3-hydroxybutanoic acid (Bu) was determined by methanolysis and trifluoroacetylation followed by GC-MS analysis on a Lipodex A chiral column (Macherey-Nagel, Düren, Germany). Hermansson K et al. (1993) *Eur J Biochem* 212:801-9.

GC-MS Analysis. All analyses were performed on an HP 6890/5973 GC-MSD spectrometer (Hewlett Packard, Wilmingtdn, Del.) with a capillary DB17 column (J&W Scientific, Folsom, Calif.). Mass detection was obtained by electron ionization at 70 eV, and ions were scanned from 45 to 550 m/z.

Mild Base Treatment. This method was used to identify whether Bu is linked to the polysaccharide through an ether or ester bond, since only the latter is susceptible to mild base cleavage. A 2-mg sample of PS A2 was treated with 0.5 mL of 0.5 M NaOH at room temperature for 2 hrs, dialyzed extensively against water, and lyophilized. The sample was then examined by $^1$H NMR spectroscopy.

NMR Spectroscopy. Nuclear magnetic resonance (NMR) experiments were performed on Varian Unity 500 and Unity Plus 750 spectrometers (Varian, Palo Alto, Calif.). A 10-mg sample of PS A2 dissolved in 0.7 mL of D$_2$O was used for 2D experiments. $^1$H—$^1$H double-quantum filtered correlation spectroscopy DQF-COSY; Derome A E et al. (1990) *J Magn Reson* 88;177-85), total correlation spectroscopy (TOCSY; Bax A et al. (1985) *J Magn Reson* 65:355-60), and nuclear Overhauser enhancement spectroscopy NOESY; Bodenhausen G et al. (1984) *J Magn Reson* 58:370-88) were carried out with standard pulse sequences provided by Varian. A spectral width of 10 ppm in each dimension was used, and mixing times of 80 and 100 ms were employed for NOESY. Spin-lock times were 50, 80, and 100 ms for various TOCSY experiments. $^1$H—$^{13}$C heteronuclear multiple quantum coherence (HMQC; Bax A et al. (1986) *J Magn Reson* 67:565-9), distortionless enhancement by polarization transfer (DEPT)-HMQC (Bendall MR et al. (1981) *J Am Chem Soc* 103:4603-5), and heteronuclear multiple bond coherence (HMBC; Lerner L et al. (1987) *Carbohydr Res* 166:35-46) spectra were recorded with proton and carbon spectral widths of 10 and 200 ppm, respectively. HMQC spectra were obtained with and without carbon decoupling. The latter was used to determine $^1J_{C,H}$ coupling constants for the anomeric carbons. Spectra were generally acquired at 70° C. NOESY spectra were also measured at 37° C. $^1$H chemical shifts were referenced to the water resonance at 4.36 ppm as calibrated externally. $^{13}$C chemical shifts were referenced to an external CH$_3$I standard at 22.5 ppm.

Structure Calculation. All calculations were performed on an Orion 200 workstation equipped with two R12000 270-MHz and two R10000 180-MHz IP27 CPUs (Silicon Graphics, Mountain View, Calif.). The Insight II 2000 program package (Molecular Simulations, San Diego, Calif.) was used for visualization, modeling, force-field calculations, energy minimizations, and molecular dynamics simulations. Surface renderings and qualitative Poisson-Boltzmann electrostatic calculations were carried out with GRASP (Nicholls A et al. (1991) *Proteins* 11:281-96) and SPOCK. Christopher J A (1998) *SPOCK: The Structural Properties Observation and Calculation Kit,* Center for Macromolecular Design, Texas A&M University, College Station, Tex. The consistent valence force field (CVFF) with harmonic potential function and including cross-terms was used for all calculations. Martin-Pastor M et al. (2000) *Biochemistry* 39:4674-83. The Polak-Ribiere conjugate gradient method was employed for minimizations after the initial 50 steps of steepest descent. As described below, each repeatingunit of PS A2 contains five monosaccharides (residues a-e) and a dual-charge motif composed of a free amnino and a carboxylic acid. Generally, residues a and c were treated uncharged for simulations in vacuo and charged for simulations in water. Individual models of each of the five sugars in one repeating unit were energy minimized in vacuo ($\epsilon$=4·r, no cutoff, final convergence<0.001 kcal·mol$^{-1}$·Å$^{-1}$). $\Phi_H$-$\Psi_H$ total energy maps for each of the five glycosidic bonds were obtained by systematically rotating both angles from 0° to 360° with 10° increments. For every linkage, each of the 36$^2$ disaccharide structures was minimized in vacuo ($\epsilon$=4·r, no cutoff, final convergence <0.001 kcal·mol$^{-1}$·Å$^{-1}$), while ($\Phi_H$ and $\Psi_H$ were restrained (cosine restraint with k=1000 kcal·mol$^{-1}$). $\Phi_H$ and $\Psi_H$ are defined as H1-C1-O1-CX' and C1-O1-CX'-HX', respectively. Homans S W (1990) *Biochemistry* 29:9110-8. Inspection of the energy landscapes allowed the identification of global minima for each pair of $\Phi_H$ and $\Psi_H$ as the following (linkages in parentheses): −36°, 35° (ac); −52°, 1° (cd); −27°, −21° (de); 42°, 3° (be); and 57°, −11° (ea). These conformations were confirmed by starting from various glycosidic dihedral angles and demonstrating convergence towards the global minima upon minimization. The torsion angle parameters were used to build an initial model of four repeating units. All observed interresidue NOE distance restraints were added to the model in the form of a flat-bottomed energy term with a proximal target value of 1.8 Å and distal target values of 3.3 Å for strong and 5.0 Å for weak NOE cross-peaks, respectively. The force constants were set to 100 kcal·mol$^{-1}$·Å$^{-2}$ with a scaling factor of 1.

Two solvent simulation approaches were taken for structure calculation and further refinement. In the first approach, the tetramer was coated on all sides with a 15-Å-thick equilibrated water layer surrounded by a 2.5-Å-thick outer water shell that was kept fixed in space to prevent solvent evaporation (3207 mobile water molecules). The ensemble was minimized to a final convergence of <0.01 kcal·mol$^{-1}$·Å$^{-1}$ with group-based summation (9.5 Å cutoff, 1.0 Å spline, 0.5 Å buffer) and $\epsilon$=1. In the second approach, the tetramer was immersed in an equilibrated water box of dimensions 60×30×30 Å$^3$ (1571 water molecules), and the system was set up as a periodic boundary condition simulation with group-based summation (15.0 Å cutoff, 2.0 Å spline, 1.0 Å buffer) and $\epsilon$=1. To equilibrate the water box further, the tetramer was constrained in space, and only water molecules were allowed to move. Minimization was carried out for 1000 steps. The constraint was then released, and further minimization was performed for 500 steps. At this stage, both 10-ps and 300-ps NOE-restrained molecular dynamics simulations of the entire equilibrated ensemble were started. The system was kept at constant volume and 298±10° K by the Andersen method as implemented in Discover 98.0 (Molecular Simulations). Time steps of 1.0 fs and the Verlet velocity integration method were used. The ensembles were minimized to <0.01 kcal·mol$^{-1}$·Å$^{-1}$.

Results

Figure 2:
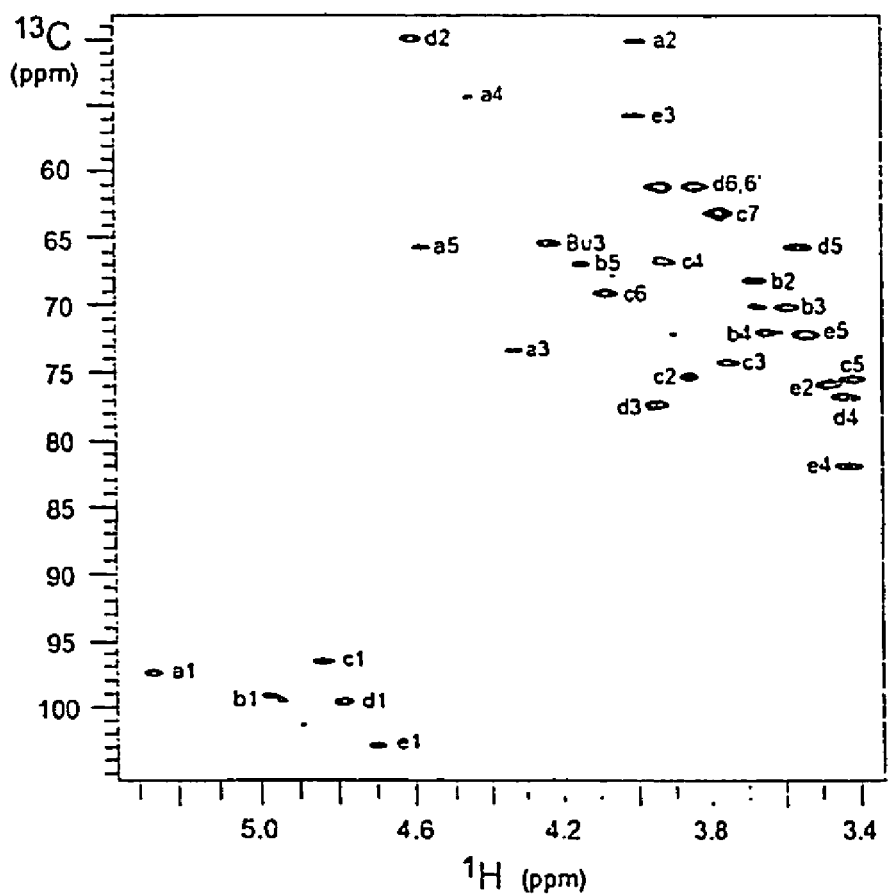
FIG. 2 is a graph depicting the $^1$H—$^{13}$C HMQC spectrum of PS A2. Each cross-peak corresponds to a C—H pair. Note that a1 refers to position 1 of residue a. Unlabeled peaks are due to contaminants.

Composition of PS A2. The components of PS A2, as identified by chemical derivatization and GC-MS analysis, are L-Fuc, D-ManNAc, D-Hep, D-ADG, 2-amnino-4-acetamido-2,4,6-trideoxy-D-galactose (D-AAT), and (S)-Bu. The exact structures and substituents of these components were further established and confirmed by NMR spectroscopy. The $^1$H NMR spectrum (FIG. 1) of PS A2 reveals five anomeric proton signals at 5.26, 4.97, 4.84, 4.79, and 4.70 ppm. They are correlated with five carbon resonances at 98.41, 100.18, 97.43, 100.48, and 103.81 ppm, respectively, as shown in the $^1$H—$^{13}$C HMQC spectrum of PS A2 (FIG. 2). These chemical shifts are characteristic of anomeric protons and carbons of pyranoses. Gorin P A (1981) *Adv Carbohydr Chem Biochem* 38:13-104. The five monosaccharides of PS A2 are designated as residues a, b, c, d, and e, according to their proton chemical shifts (FIG. 1). The complete $^1$H and $^{13}$C chemical shifts of all components were determined by 2D NMR spectroscopy as described below.

Assignment of Residue a (α-D-AAT). The chemical shifts of all six protons of this residue were readily obtained from the $^1$H—$^1$H DQF-COSY spectrum of the polysaccharide (not shown). Since only protons attached to adjacent carbons show correlation in a COSY spectrum, a proton chemical shift can be determined once the adjacent proton in a sequence has been assigned. Starting from the known anomeric resonance, this strategy was used to trace all six protons in the sugar ring. Since H1 (δ5.26 ppm) displays a cross-peak with a resonance at 3.99 ppm, the latter was unambiguously assigned to H2. The H2 signal also shows a cross-peak with a signal at 4.32 ppm, which is obviously due to H3. Similarly, H3 correlates with a signal at 4.46 ppm, which was assigned to H4. Furthermore, H4 correlates with a resonance at 4.59 ppm (H5), and H5 has a cross-peak with a signal at 1.10 ppm (H6). The complete proton chemical shift assignment was thus obtained (Table 1).

mido group at C4. The latter was confirmed by the three-bond correlation between H4 and the acetamide carbonyl carbon (δ175.51 ppm) in the $^1$H—$^{13}$C HMBC spectrum of PS A2.

Figure 3:
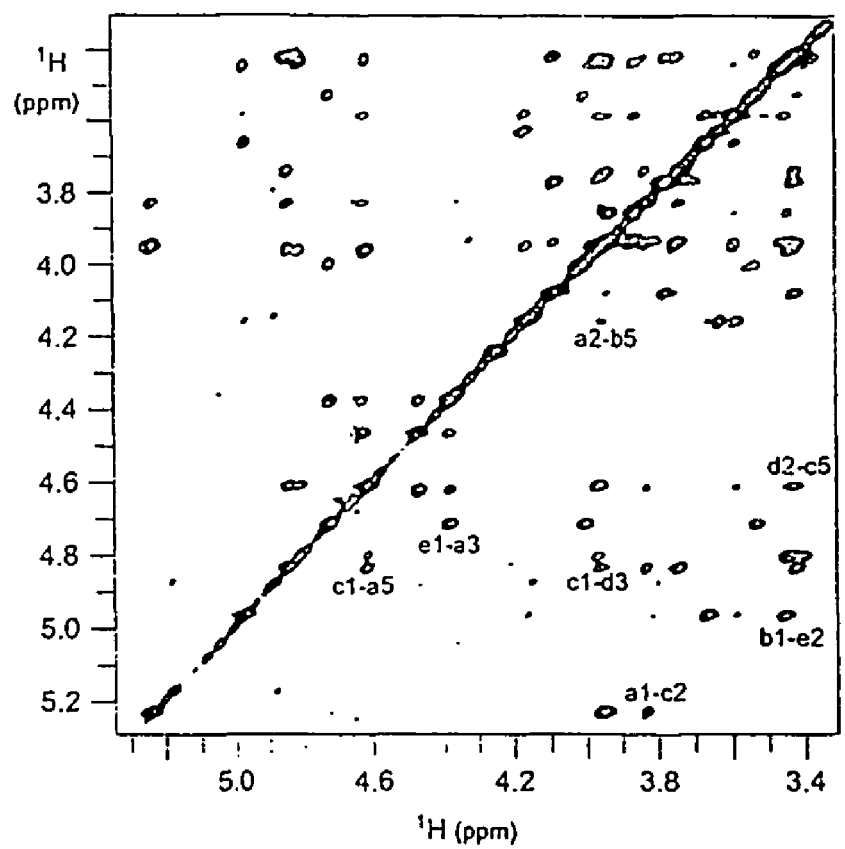
FIG. 3 is a graph depicting the $^1$H—$^1$H NOESY spectrum of PS A2 recorded at 37° C. and 750 MHz field strength. The methyl proton region is not shown. Seven interresidue NOE cross-peaks are labeled. Note that a1-c2 refers to the correlation between H1 of residue a and H2 of residue c.

Based on the compositional analysis by GC-MS, residue a is expected to assume a galacto configuration. This conclusion is supported by intraresidue NOEs (nuclear Overhauser effects) obtained from the $^1$H—$^1$H NOESY spectrum of PS A2 (FIG. 3). H4 displays strong NOEs to both H3 and H5, which indicates that H4 is in close proximity to and thus on the same side of the sugar ring as H3 and H5. Furthermore, residue a adopts an α-configuration at its anomeric center, which is evident from the down-field chemical shift of H1 (δ5.26 ppm, singlet) as well as the characteristic $^3J_{H1,H2}$ (<3 Hz) and $^1J_{C1,H1}$ (194 Hz) coupling constants. Gorin P A (1981) *Adv Carbohydr Chem Biochem* 38:13-104. Combination of these data identified residue a as 2-amino-4-acetamido-2,4,6-trideoxy-α-D-galactopyranose.

Assignment of Residue b (α-L-Fuc). The assignment of proton resonances was not as straightforward as in the case of residue a. Starting from the H1 resonance at 4.97 ppm, H2 (δ3.69 ppm) and H3 (δ3.59 ppm) were assigned according to the H1-H2 and H2-H3 DQF-COSY cross-peaks. However, as no H3-H4 correlation is observable in the DQF-COSY, the assignment of H4 relies on the total correlation originating from H1. In the TOCSY spectrum, H1 correlated with a total of three signals at 3.69, 3.59, and 3.65 ppm, respectively. Since the first two originate from H2 and H3, the third resonance has to stem from H4. In the NOESY spectrum of PS A2 (FIG. 3), both H3 and H4 correlate with a signal at 4.14 ppm, and H2 shows an NOE to a signal at 1.17 ppm. These two protons (δ4.14 and 1.17 ppm) are in close proximity to H2, H3, and H4 of residue b. Thus, they are also located on this residue. Furthermore, since the signals at 4.14 and 1.17 ppm correlate with each other in both the DQF-COSY and TOCSY spectra, they were assigned to H5 and H6, respectively. On

TABLE 1

Complete $^1$H and $^{13}$C chemical shift assignments of PS A2 residues*

| Residue | | 1 | 2 | 3 | 4 | 5 | 6 | 7 | NAc** (C=O) |
|---|---|---|---|---|---|---|---|---|---|
| a →3)-α-D-AATp-(1→ | $^1$H | 5.26 | 3.99 | 4.32 | 4.46 | 4.59 | 1.10 | | |
| | $^{13}$C | 98.41 | 50.92 | 74.25 | 55.27 | 66.56 | 17.08 | | 175.51 |
| b α-L-Fucp-(1→ | $^1$H | 4.97 | 3.69 | 3.59 | 3.65 | 4.14 | 1.17 | | |
| | $^{13}$C | 100.18 | 69.06 | 71.02 | 72.97 | 67.80 | 16.87 | | |
| c →2)-α-D-Hepp-[6→Bu]-(1→ | $^1$H | 4.84 | 3.85 | 3.75 | 3.92 | 3.41 | 4.08 | 3.77 | |
| | $^{13}$C | 97.43 | 76.21 | 75.17 | 67.69 | 76.33 | 70.03 | 64.03 | |
| d →3)-β-D-ManNAcp-(1→ | $^1$H | 4.79 | 4.60 | 3.95 | 3.56 | 3.44 | 3.84, 3.94 | | |
| | $^{13}$C | 100.48 | 50.85 | 78.24 | 66.65 | 77.77 | 61.97 | | 175.67 |
| e →4)-β-D-ADGp-[2→](1→ | $^1$H | 4.70 | 3.48 | 4.01 | 3.43 | 3.54 | 1.29 | | |
| | $^{13}$C | 103.81 | 76.83 | 56.60 | 82.84 | 73.11 | 18.14 | | 175.68 |
| Bu-(3→ | $^1$H | | 2.56 | 4.23 | 1.26 | | | | |
| | $^{13}$C | 175.42 | 45.99 | 66.34 | 23.02 | | | | |

*Chemical shifts are reported in ppm.
**The methyls in all three NAc groups have the same chemical shifts: $\delta_H$ 2.05 ppm and $\delta_C$ 23.41 ppm.

Once the protons had been identified, the chemical shifts of their corresponding carbons were readily determined from heteronuclear correlations between carbon and proton in C—H pairs. As revealed by the $^1$H—$^{13}$C HMQC spectrum (FIG. 2), C1-C6 of residue a appear at 98.41, 50.92, 74.25, 55.27, 66.56, and 17.08 ppm, respectively. The chemical shifts of both H6 (δ1.10 ppm) and C6 (δ17.08 ppm) indicate that the 6-position bears a methyl group. The chemical shift of C2 (δ50.92 ppm) is characteristic of a carbon substituted with an amine, whereas that of C4 (δ55.27 ppm) suggests an acetathe basis of the proton assignments, the chemical shifts of C1-C6 were readily obtained from the $^1$H—$^{13}$C HMQC spectrum (FIG. 2 and Table 1).

Although H5 and H6 were initially assigned with certain ambiguity, they were confirmed by multiple-bond H—C correlations from the HMBC spectrum. The three-bond correlations between H1 and C5, H5 and C4, and H6 and C5 unambiguously show that H5 and H6 are located on residue b. Both carbon and proton chemical shifts (Table 1) are typical of 6-deoxyhexopyranose. Since L-Fuc was the only such sugar identified by GC-MS analysis, residue b had to be the fucose. Moreover, H1 appears as a singlet ($^3J_{H1,H2}$<3 Hz) in the $^1$H-NMR spectrum (FIG. 1), and the $^1J_{C1,H1}$ is 185 Hz. Both values indicate an α-configuration at the anomeric center. Thus, residue b was identified as α-L-fucopyranoside.

Assignments of Remaining Residues. Using similar approaches, the complete proton and carbon chemical shifts of the remaining residues were obtained (Table 1). The chemical shifts identify residues c, d, and e as Hep, ManNAc, and ADG, respectively. The $^1J_{C1,H1}$ coupling constants for residues c and d are 168 and 171 Hz, respectively, which indicates an α-configuration at the anomeric centers. Janeway C A Jr et al. (1994) *Immunobiology* (Garland Publishing, New York, N.Y.), pp. 4:1-4:35. H1 (4.70 ppm) of residue e appears as a doublet with a $^3J_{H1,H2}$ of 8 Hz (FIG. 1), which strongly indicates a β-configuration at the anomeric center.

Sequence Determination. The next task was to determine the linkage positions and sequence of the polymer. Such information can be obtained directly from long-range $^1$H—$^{13}$C correlations across the glycosidic bond between two residues. Lemer L (1987) *Carbohydr Res* 166:35-46. The HMBC spectrum of PS A2 reveals a cross-peak with $\delta_H$ 3.85 ppm and $\delta_C$ 98.41 ppm, which arises from H2 of residue c (H2c) and C1 of residue a (C1a) and corresponds to a three-bond coupling across the glysidic linkage H2c-C2c-O1a-C1a. Therefore, residues c and a are connected, and the linkage involves position 1 of residue a and position 2 of residue c, thus establishing a fragment with the sequence of a-(1→2)-c. Similarly, since H1c ($\delta_H$ 4.84 ppm) and C3d ($\delta_C$ 78.24 ppm) display a cross-peak in the HMBC spectrum, residues c and d are connected in a c-(1→3)-d sequence. A d-(1→4)-e fragment is indicated by the correlation between $C_1$d and H4e. Furthermore, residue e is linked to residue a in the form of e-(1→3)-a, as established from the long-range correlation between H1e and C3a.

Connecting the above fragments yields a linear sequence of a-(1→2)-c-(1→3)-d-(1→4)-e-(1→3)-a. Therefore, the fundamental building unit c-d-e-a repeats itself to produce the backbone of the polymer. In addition, residue b is connected to e via a 1→2 linkage as indicated by the correlation between C1b and H2e. Residue e is connected with residues a, b, and d and forms a branching point in the structure. Thus, the repeating unit of PS A2 is a branched pentasaccharide with the sequence of →2)-c-(1→3)-d-(1→4)[b-(1→2)]-e-(1→3)-a-(1→. Furthermore, Hep (residue c) is substituted with Bu through an ether linkage between the C3 of Bu and C6 of c. The linkage position is confirmed by the long-range correlation between C3 of Bu and H6c in the HMBC spectrum. The observation that Bu is not susceptible to mild base treatment strongly supports ether instead of ester linkage. The chemical structure of PS A2 was thus completely determined and is shown in FIG. 4.

NOE Distance Restraints. A total of 41 intraresidue and 10 interresidue NOE cross-peaks per repeating unit are observed (FIG. 3). Intraresidue NOEs were used to determine the absolute configurations of the individual residues a-e. Interresidue NOEs were incorporated into the global structure calculation as distance restraints. NOE cross-peak intensities were classified as either strong (s) or weak (w) and interpreted as 1.8-3.3 Å and 1.8-5.0 Å distance intervals, respectively. The detected interresidue NOEs are the following: c1-a5 (s), c2-a1 (s), c1-d3 (s), c5-d2 (s), d1-e6 (s), d2-e6 (w), e1-a3 (s), e2-b1 (s), a2-b5 (w), and a2-b6 (w). The last two NOEs occur between non-adjacent residues. It is noteworthy that by itself the initial model of four repeating units based on $\Phi_H$-$\Psi_H$ grid searches already satisfies eight interresidue distances perfectly with the remaining two being close to target values.

Figure 5:
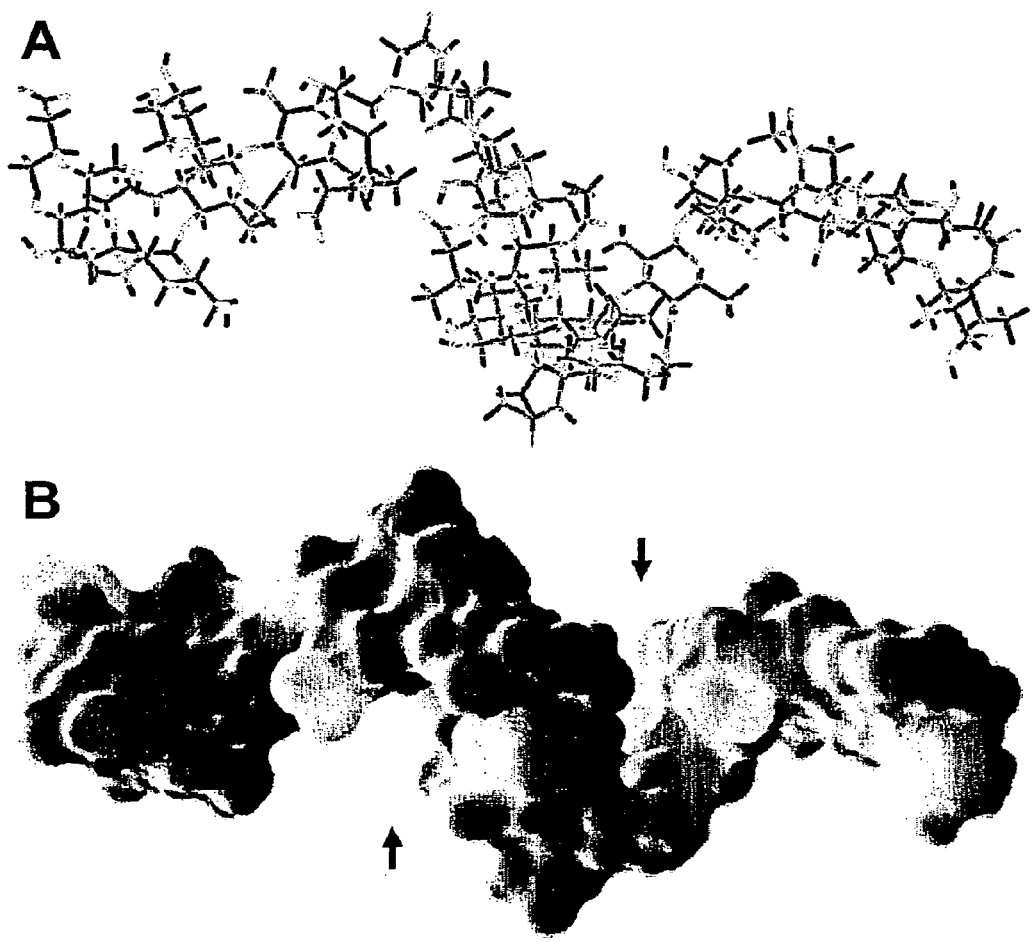
FIG. 5 is a pair of graphics depicting (A) a stick model of the helical structure of one tetramer (four repeating units) of PS A2, and (B) an electrostatic surface representation of the tetramer. In (A) carbons are colored green, oxygens red, nitrogens blue, and hydrogens white. In (B) positive charges are colored blue, negative charges are colored red, and two grooves are indicated by arrows. Both models are oriented identically, with the left sides tilted slightly towards the observer to make all eight charges visible simultaneously.

Three-Dimensional Structure of PS A2. Preferred solution conformations of one tetramer (four repeating units) of PS A2 were computed by energy mininmization from NOE-restrained molecular mechanics and dynamics calculations. The final models were in excellent agreement and consistent with all intra- and interresidue NOE cross-peak. The tetramer describes a right-handed helix with two repeating units per turn and a pitch of 20 Å (FIG. 5). The molecule is covered with a high density of charges, as illustrated by the electrostatic surface representation (FIG. 5B). All charges are exposed on the outmost surface of the molecule and are in favorable positions for binding interactions. Positive and negative charges alternate along the sides of the helical chain and follow a zigzag pattern with approximately equal distances of 10 Å. The helix is characterized by a regular series of grooves that are oriented roughly perpendicular to its long axis. These grooves are about 10 Å wide, 10 Å long, and 5 Å deep. All four edges of a specific groove are occupied by charges from residues $a_{x-1}$ (amine), $c_x$ (carboxylate), $a_x$ (amine), and $c_{x+1}$ (carboxylate), respectively, where x denotes a given repeating unit. The first charge projects towards the outside of the groove, whereas the other three face towards the inside. The tetramer contains two complete grooves formed between repeating units 1-3 and 2-4, respectively, as counted from left to right (arrows in FIG. 5B).

Figure 6:
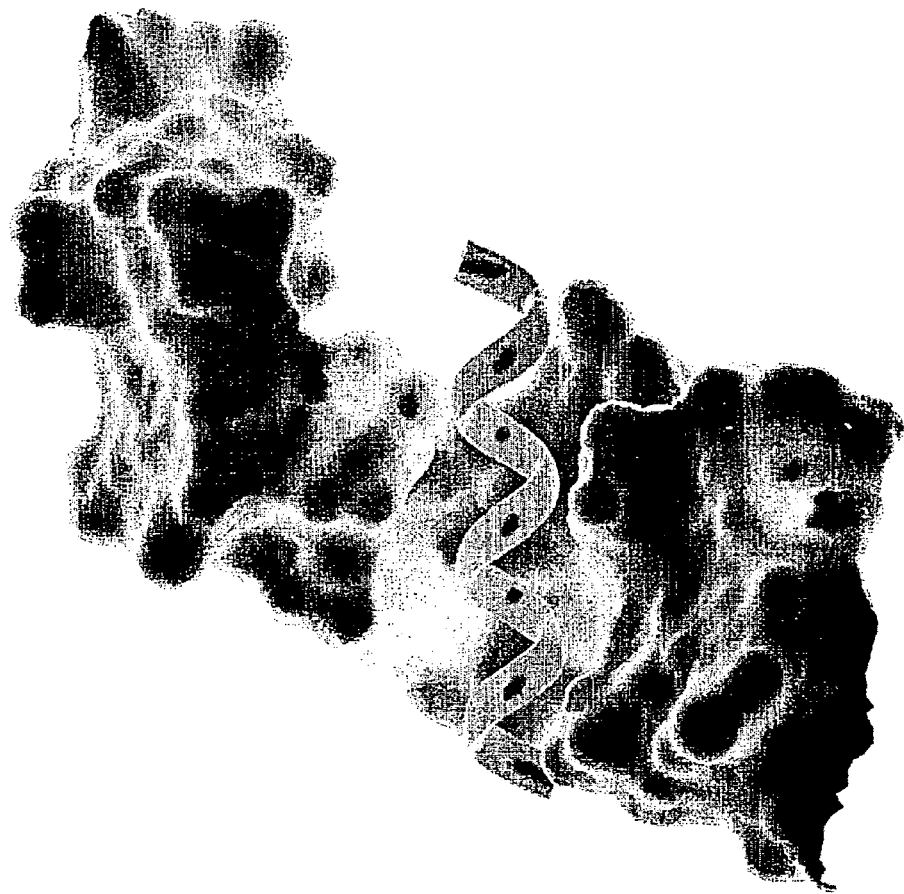
FIG. 6 is a graphic depicting a model of a protein a helix bound to one of the PS A2 grooves. The electrostatic surface of PS A2 is shown within 15 Å of the helix. The helix is represented by a ribbon, and the coloring scheme for the surface is identical to that in FIG. 5B.

Models for the Structure-Activity Relationship in ZPSs. The conformational model of PS A2 suggests plausible mechanisms for the interaction of ZPSs with other molecules. In one scenario, PS A2 binds to other molecules primarily "along its sides", which display a high density of alternating opposite charges (see above). High binding affinities would be achieved via abundant electrostatic interactions supplemented by the potential for numerous hydrogen bonds to hydrophilic hydroxyls and, to a lesser extent, van der Waals interactions. In another scenario, the grooves of PS A2 serve as the primary binding domains. The geometry of each groove would be able to accommodate the insertion of an α helix from a protein. To test this idea, hypothetical α helices (10-14 mers) with charged side chains at their termini were docked into PS A2 grooves in silico and found to fit very well (FIG. 6). The charges at the edges of a groove may help anchor the peptide. In addition to multiple salt bridges, the complex may be stabilized by primarily hydrophobic interactions along the inner surface of the groove. In either of these scenarios, charged groups located at critical positions contribute significantly to binding, which would explain why charges are essential determinants of the biological activity of ZPSs.

The "groove-binding model" offers an attractive explanation for the T-cell-stimulating activity of ZPSs. In general, T-cell activation is initiated by the specific recognition of antigens bound to major histocompatibility (MHC) molecules on antigen-presenting cells. The physical binding of T-cell receptors to antigen-MHC complexes triggers specific T-cell responses to infectious microorganisms. Janeway C A Jr et al. (1994) in *Immunobiology* (Garland, New York, N.Y.), pp 4:1-4:35. Crystallographic studies have revealed that α helices form the lateral boundaries of antigen-binding clefts in MHC molecules. Stem L J et al. (1994) *Nature* 368:215-21; Reinherz E L et al. (1999) *Science* 286:1913-21. In this regard, it is possible that PS A2 forms a complex with MHC molecules by capturing α helices in its grooves. It is noteworthy that PS A2 is polymeric, with hundreds of repeating units, and thus provides a large number of binding sites. Furthermore, PS A2 may cross-link T-cell receptors and MHC molecules by clamping α helices on both proteins.

In support of the groove binding model believed to explain the observed immunomodulatory effects of the zwitterionic polysaccharides, physicochemical measurements based on microcalorimetry, solution phase NMR, BIACore, and affinity chromatography involving PS A2 and class II MHC are consistent with the model.

Measurement of Binding Between ZPSs and Peptide Fragments of MHC Molecules.

Isothermal titration calorimetry (ITC). When two molecules bind, heat is either released or absorbed in direct proportion to the amount of binding that occurs. Measurement of this heat allows accurate determination of the binding association constant ($K_a$), stoichiometry (N), and enthalpy ($\Delta H$) and entropy ($\Delta S$) contributions to the Gibbs free energy ($\Delta G$) of association.

An 18-mer peptide fragment from the murine MHC-II IA β1 domain (PIIb1) with the sequence of Ac-Ala-Glu($^-$)-Tyr-Tyr-Asn-Lys($^+$)-Gln-Tyr-Leu-Glu($^-$)-Gln-Thr-Arg($^+$)-Ala-Glu($^-$)-Leu-Asp($^{-1}$)-Thr-$NH_2$ was chemically synthesized. This fragment is part of the lateral α-helical boundary of the peptide-binding groove on MHC. To test the binding between MHC peptides and polysaccharides, a number of ITC experiments were performed. All experiments were carried out on a VP ITC instrument (MicroCal, Northampton, Mass.). In a typical experiment, 5- or 10-μl aliquots of polysaccharides (0.02 mg/ml) were injected into 1.4 ml of peptide (0.015 mg/ml) solution with rapid mixing at 300 rpm. There were 4 min intervals between each injection. Both polysaccharides and peptides were dissolved in 10-mM PBS buffer, pH 7.2.

Peptide PIIb1 showed strong binding to PS A2 and the type 1 capsular polysaccharide of *Streptococcus pneumoniae* (CP1). The control peptide (Lys-Asp)$_{15}$ did not show binding to PS A2 or CP1. The control polysaccharide, type III capsular polysaccharides from group B Streptococcus (GBS), did not show binding to peptide PIIb1.

Circular dichroism (CD). Upon complexation, the peptide and/or the polysaccharide may undergo conformational changes. This phenomenon has been observed previously for the binding of specific peptides to heparin. To test whether our peptides undergo conformational changes, we have used CD spectroscopy to assess both free and bound peptides. All CD spectra were recorded on a AVIA CD spectrometer (AVIA, Lakewood, N.J.). Polysaccharides and peptides were prepared as 1 mg/ml solution in 10 mM PBS, pH 7.2. CD spectra were obtained on both peptide and polysaccharide alone, and then 5 μl aliquots of polysaccharides were titrated into the peptide solution and CD spectra were recorded on the mixtures. The spectra in the region 240-190 nm were analyzed to determine the fractional percentages of secondary structural elements. These ongoing studies will verify whether our polysaccharides preferentially bind and stabilize α-helical peptides.

Figure 7:
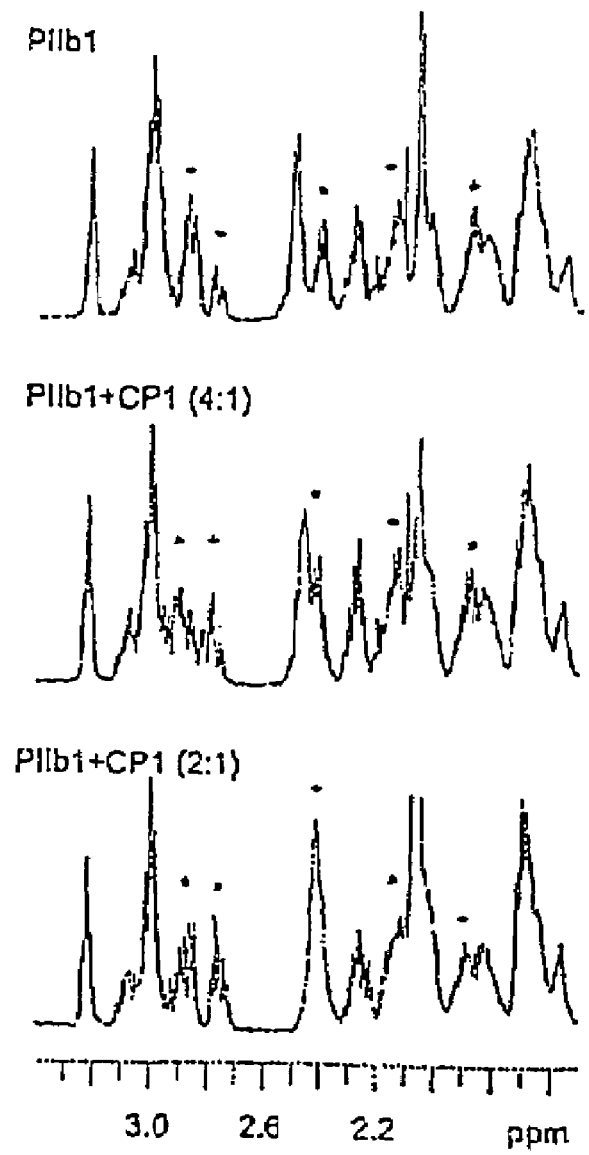
FIG. 7 is a graph depicting NMR chemical shift displacement upon addition of CP1 to the 18-mer fragment of murine MHC-II IA β1 (PIIb1).

NMR spectroscopy. To determine the binding sites between peptide PIIb1 and CP1, CP1 was titrated into the peptide solution and the proton chemical shift changes observed. The addition of CP1 to PIIb1 caused chemical shift displacement in several signals, most notably, the side chain protons of the aspartic acid residue (see FIG. 7). As a control, CP14 (*Streptococcus pneumoniae* type 14 capsule, a neutral polysaccharide) was titrated to PIIb1. Only after the addition of a large amount of CP14 was there observed a slight chemical shift change in one signal. Similar titration experiments can be used to obtain the stoichiometry of the interaction.

Example 2

Sp1

*S. pneumoniae* type 1 polysaccharide (Sp1) (Tzianabos A O et al. (1993) *Science* 262:416-9) shares the same T-cell activity and the consequent ability to regulate bacterial abscess formation as tested in rat model of intraabdominal abscesses (Tzianabos A O et al (2000) *J Biol Chem* 275:6733-40; Lindberg B et al (1980) *Carbohydr Res* 78:111-7). Sp1 is a linear polymer consisting of trisaccharide repeating units, containing galacturonic acid (GalA, residues a and c), 2-acetoamide-4-amino-2,4,6-trideoxygalactose (Sug, residue b) with a sequence of →3)-α-D-GalA(a)-(1→3)-α-D-Sug(b)-(1→4)-α-D-GalA(c)-(1→(17, 22). Each repeating unit of Sp1 contains one positively charged amine and two negatively charged carboxyl groups.

Purification of Sp1. Crude PS extract from type 1 *S. pneumoniae* was purchased from the American Type Culture Collection (Atlanta, Ga.). A 20 mg sample of the crude material was dissolved in 1.5 mL of 2M NaOH and heated at 80° C. for 3 hrs in order to degrade the contaminating ribitol-phosphate teichoic acids. Jennings H J et al. (1980) *Biochemistry* 19:4712-9; van Dam J E G et al. (1990) *Antonie van Leewenhoek* 58:1-47. The mixture was then neutralized with 2M HCl, dialyzed extensively against deionized water, and lyophilized. The product was then purified on a Sephacryl S300 column (Amersham Pharmacia Biotech, NJ), eluting with phosphate buffered saline (0.01 M phosphate, 0.15 M NaCl, pH 7.24) containing 0.05% azide. Fractions were monitored by a refractive index detector for carbohydrate and a UV detector at 280 nm for contaminating proteins. Sp1 eluted close to the void volume of the column and had an average molecular mass of 100 kDa. Sp1 fractions were pooled, dialyzed extensively against deionized water, and lyophilized. Its structure and purity were verified by NMR analysis.

NMR Spectroscopy. All NMR spectra were obtained from a sample of 8 mg of purified Sp1 which was exchanged with $D_2O$ once and redissolved in 0.7 mL of $D_2O$. NMR experiments were performed at 37° C. on a Varian Unity500 instrument. $^1H$ chemical shifts were referenced to the water resonance at 4.36 ppm as calibrated externally. $^{13}C$ chemical shifts were referenced to an external $CH_3I$ standard at 22.5 ppm. Most spectra were obtained in the phase-sensitive TPPI mode with standard pulse sequences. Sanders J K M et al., *Modern NMR Spectroscopy*, 2nd ed., 1993, Oxford Press; Braun S et al., 150 *and More Basic NMR Experiments*, 1998, Wiley-V C H. $^1H$—$^1H$ TOCSY (Bax A et al. (1985) *J Magn Reson* 65:355-60), DQF-COSY Piantini U et al. (1982) *J Am Chem Soc* 104:6800-1), and NOESY (Bodenhausen G et al. (1984) *J Magn Reson* 58:370-88) were recorded with a spectra width of 10 ppm at both dimensions. A spin-lock time of 80 ms was used for TOCSY. NOESY spectra were recorded at mixing times of 25, 50, 75, and 100 ms, respectively. NOE cross peaks were integrated according to the same integration limit for each spectrum. $^3J_{H,H}$ couplings were measured from DQF-COSY and E.COSY. Griesinger C et al. (1987) *J Magn Reson* 75:474-92. $^1H$—$^{13}C$ HMQC (Bax A et al. (1986) *J Magn Reson* 67:565-9), $^1H$—$^{13}C$ HMBC (Bax A et al. (1986)

*J Am Chem Soc* 108:2093-4) were recorded with 100 and 180 ppm at the carbon dimension, respectively. HMQC spectra were recorded with and without $^{13}$C decoupling during the acquisition. The latter was used to extract $^1J_{CH}$ coupling constants. Data were processed with either VNMR or NMRPipe. Generally a data matrix of 512×2048 was obtained and zero-filtered to 1024×2048 in the processing. Sine-bell or other window functions were applied in both $t_1$ and $t_2$ dimensions corresponding to the digital resolutions. Spectra were phase corrected and baseline flattened.

Molecular Modeling. Molecular mechanics and dynamics calculations were carried out with the INSIGHT II 2000/Discover program (Accelrys, San Diego, Calif.) on an Octane workstation with a R10000 195 MHz central processing unit (Silicon Graphics, Mountain View, Calif.). The consistent valence force field (CVFF) with harmonic potential function and cross terms (Hagler A T et al. (1979) *J Am Chem Soc* 101:5122-30) was used for all calculations since it yielded consistent results in the grid-search of various disaccharide conformations in both charged and uncharged forms. No cutoff was imposed on the calculation of non-bonded interactions. All calculations were performed in vacuo with a distance dependent dielectric constant ($\epsilon=4\cdot r$) unless otherwise specified. Surface renderings and quantitative Poisson-Boltzmann electrostatic calculations were carried out with GRASP (Nicholls A et al. (1991) *Proteins* 11:281-96) and SPOCK (Christopher J A (1998) *SPOCK: The Structural Properties Observation and Calculation Kit* (Center for Macromolecular Design, Texas A&M University, College Station, Tex.).

Monosaccharide Model Building. Molecular models of the three monosaccharide residues of Sp1 were built with the Biopolymer module of the INSIGHT II 2000 program. The free amine in residue b and the carboxylic acids in residues a and c were treated uncharged. The initial model of each monosaccharide was energy minimized by steepest descent until the maximum derivative was less than 1000.0 kcal·mol$^{-1}\cdot$Å$^{-1}$, followed by Polak-Ribiere conjugate gradient method until the maximum derivative was less than 10.0 kcal·mol$^{-1}\cdot$Å$^{-1}$ and Newton minimization algorithm (BFGS) until the maximum derivative was less than 0.001 kcal·mol$^{-1}\cdot$Å$^{-1}$.

Grid-Search. The conformational preference for each of the three glycosidic linkages of the Sp1 repeating unit was assessed by systematic grid-searches of the $\Phi_H$ and $\Psi_H$ dihedral angles. $\Phi_H$ and $\Psi_H$ are defined as H1-C1-O1-CX' and C1-O1-CX'-HX', respectively, whereas X' refers to the glycosidic linkage site. $\Phi_H$-$\Psi_H$ total energy maps were obtained by systematically rotating both angles from −180° to 180° with 10° increments. For every linkage, each of the 36$^2$ disaccharide structures was energy minimized with the same method as described above for the monosaccharides, while the $\Phi_H$ and $\Psi_H$ dihedral angles and chair conformation of pyranose rings were restrained (cosine restraints with k=1, 000 kcal·mol$^{-1}$). The lowest energy conformation in each energy map was selected to build the corresponding disaccharide and the structure was further energy minimized. This step of refinement was used to verify the accuracy of the grid-search. To evaluate the charge contribution, the amine in residue b and the carboxylate groups in a and c were treated uncharged and charged in separate calculations. When treated uncharged, a distance-dependent dielectric constant $\epsilon=4r$ was used. When treated charged, $\epsilon=4r$, 80, and 80r were examined.

Restrained Energy Minimization. An initial molecular model of four repeating units (4 RU, containing 12 monosaccharides) of Sp1 was built with the preferred dihedral angles obtained from the grid-search calculations. To limit structural bias, linear and random conformations were also built as the initial models. All observed interresidue NOE distance restraints were added to the initial model in the form of a flat-bottomed energy term with a proximal target value of 1.8 Å, and distal target values of 3.3 Å for strong and 5.0 Å for weak NOE crosspeaks, respectively. The force constants were set to 100 kcal·mol$^{-1}\cdot$Å$^{-2}$ with a scaling factor of 1. The molecular model was energy minimized by steepest descent method until the maximum derivative was less than 1000.0 kcal·mol$^{-1}\cdot$Å$^{-1}$, followed by Polak-Ribiere conjugate gradient method until the maximum derivative was less than 0.001 kcal·mol$^{-1}\cdot$Å$^{-1}$.

Restrained Molecular Dynamics. To refine the structure, molecular dynamics (MD) simulations of the Sp1 4 RU with NOE restraints were performed. The energy minimized structure was used as starting geometry for the MD simulation. Simulated annealing simulations were carried out for 5 cycles from 700 to 300 K at 10 K per 5 ps. The final structures were fully minimized at 300 K until final convergence <0.001 kcal·mol$^{-1}\cdot$Å$^{-1}$. Constant NVT MD calculation was performed using the Verlet velocity algorithm with a 1.0 fs time step at 300 K. Temperature was controlled by velocity scaling in equilibration phase and Andersen algorithm in production phase with a collision ratio of 1.0. The system was equilibrated for 10 ps and the production run was carried out for 500 ps. As the potential energy stabilized in less than 10 ps, the equilibration phase was discarded. Intermediate structures were saved every 0.1 ps for analysis purposes.

NOE Back-Calculation. NOESY spectra were simulated from the 3D structures of Sp1 4 RU using the program MORASS (multispin Overhauser relaxation analysis and simulations) at mixing time of 75 ms. $^1J_{CH}$ values were incorporated into the NOE simulation as an autorelaxation term by the attached $^{13}$C to account for heteronuclear dipolar relaxation. Martin-Pastor M et al. (1999) *Biochemistry* 38:8045-55; Wuthrich K (1986) *NMR of Proteins and Nucleic, Acids*, John Wiley & Sons, New York; Bush C A (1994) *Methods Enzymol* 240:446-59.

Results

Chemical Shift Assignment. NMR spectroscopy with its NOE-derived distance restraints offers the possibility of obtaining the conformation of saccharides in solution. This approach requires first a complete assignment of the $^1$H and $^{13}$C resonances in the molecule. Sp1 is composed of trisaccharide repeating units with two galacturonic acid residues and a 2-acetoamide-4-amino-2,4,6-trideoxygalactose. Its primary structure was determined previously by chemical methods. Lindberg B et al. (1980) *Carbohydr Res* 78:111-7; Li Y et al. (2001) *Immunity* 14:93-104. Extensive NMR analysis of Sp1 has not been carried out and its NMR chemical shifts have not been assigned and published. In order to obtain the $^1$H and $^{13}$C chemical shifts, a combination of NMR experiments were conducted, including 1D $^1$H and 2D TOCSY, DQF-COSY, NOESY, HMQC, and HMBC. The signals were well separated and these experiments were sufficient for the unambiguous assignments as shown in Table 2. The NMR analysis and assignments also confirmed the chemical structure of Sp1.

TABLE 2

1H and 13C chemical shift assignments (in ppm) and $^1J_{CH}$ (in Hz) of Sp1

| Residue | | 1 | 2 | 3 | 4 | 5 | 6 | NAc-CH$_3$ |
|---|---|---|---|---|---|---|---|---|
| a →3)-α-D-GalA-(1→ | $^1$H | 5.07 | 3.96 | 4.02 | 4.47 | 4.13 | | |
| | $^{13}$C | 101.97 | 68.76 | 79.12 | 71.03 | 75.10 | | |
| | $^1J_{CH}$ | 173.0 | 150.4 | 145.0 | 150.4 | 144.0 | | |
| b →3)-α-D-Sug-(1→ | $^1$H | 4.99 | 4.15 | 4.27 | 3.79 | 4.76 | 1.27 | 2.04 |
| | $^{13}$C | 101.19 | 50.51 | 76.18 | 55.92 | 65.75 | 18.18 | 25.19 |
| | $^1J_{CH}$ | 176.9 | 129.3 | 146.8 | 149.5 | 149.5 | 127.9 | 130.0 |
| c →4)-α-D-GalA-(1→ | $^1$H | 5.22 | 3.93 | 4.08 | 4.39 | 4.61 | | |
| | $^{13}$C | 99.85 | 70.83 | 71.63 | 82.26 | 73.90 | | |
| | $^1J_{CH}$ | 176.3 | 149.5 | 146.8 | 148.6 | 143.1 | | |

NOE-Derived Distance Restraints. To obtain the distance constraints from NOEs, the NOESY spectra of Sp1 were acquired at mixing times of 25, 50, 75, and 100 ms, respectively. NOE cross peaks were assigned to the protons within the same monosaccharide or adjacent residues, as NOE contacts among non-adjacent residues are rarely observed in carbohydrates. A total of 24 intraresidue and 24 interresidue NOE crosspeaks per repeating unit were observed. The volumes of all these cross peaks at four mixing times were integrated and the NOE build-up curves were obtained. Most of the NOE intensities increased from 25 to 100 ms except for two that increased from 25 to 75 ms and decreased slightly at 100 ms. Since the signals at 75 ms were not influenced by spin-diffusion and also the zero-quantum coherence artifacts were at minimum, the NOE intensities at the mixing time 75 ms was used in place of the build-up curves to determine distance restraints. Wuthrich K (1986) *NMR of Proteins and Nucleic Acids,* John Wiley & Sons, New York. NOE cross-peak intensities were classified as either strong or weak and interpreted as 1.8 Å-3.3 Å and 1.8 Å-5.0 Å distance intervals, respectively. Interresidue NOE-derived restraints were incorporated into the global structure calculation.

Conformational Preference. Poly- and oligosaccharides consist of monosaccharides joined together by rotationally flexible glycosidic bonds. The global shape of an oligosaccharide depends mainly on rotational flexibility about the glycosidic linkages, whereas the intrinsic flexibility of sugar rings is rather limited and different orientations of the pendent groups have a limited influence on the conformational spaces of saccharides. To assess the conformational preferences of Sp1 due to linkages and substitution patterns of the individual glycosidic component, systematic grid-searches were performed for all its three glycosidic linkages. In this analysis, the $\Phi_H$ and $\Psi_H$ angles of each glycosidic linkage were varied independently in 10-degree increments from −180 to +180 degrees and the total energy was evaluated for each phi-psi pair. The $\Phi_H$-$\Psi_H$-energy contour map for each disaccharide was obtained. There was one energy minimal plateau for each disaccharide unit. The resulting pairs of lowest energy $\Phi_H$-$\Psi_H$ pairs were as the following (linkages in parentheses): −50°, −35° (ab); −41°, 9° (bc); −41°, −35° (ca). These conformations were confirmed by starting from various dihedral angles for each glycosidic Linkage and demonstrating convergence towards the global minima upon minimization.

Structural Calculation. The structure of Sp1 was investigated by modeling the conformation of several repeating units including a 12 mer (4 RU), 14 mer, and 18 mer. One repeating unit is generally too short to give an overall representation of the conformation of a polysaccharide. Moreover, the modeling of several repeats would remove artifacts due to the unstrained termini, thus allowing the assembly of a polymer structure by taken the parameters of the middle portion of several repeats. Preferred conformation of the 4 RU of Sp1 was computed by energy minimization with interresidue NOE distance restraints by two approaches. In the first approach, the initial model of the 4 RU was built using the phi-psi angles obtained from the grid-search and then fully minimized with NOE-derived distance constraints. In a slightly different approach, the initial models were minimized first without and then with NOE-distance constraints. These two minimization schemes gave practically the same results for the 12 mer, 14 mer, and 18 mer. The averaged phi-psi angles of ab and ca were consistent with those obtained from the disaccharide conformational grid-search. For the bc linkages, the preferred dihedral angles were close to the second lowest energy minimum in the grid-search.

Molecular dynamics. The conformation of Sp1 was refined by restrained MD simulation by incorporating all the interresidue NOE distance restraints. In the simulated annealing approach, five rounds of simulated annealing from 700 to 300 K were conducted. The conformations of the 4 RU were fully minimized at the end of each cycle. This simulation generated five different conformations. The dihedral angles of the b-c linkages showed the most flexibility, particularly the psi angles, which varied from −27.9° to 27.7°. These results showed that the ab linkage is the least and bc the most flexible linkage.

NOE back-calculation. The above calculations gave several preferred conformations of Sp1. To determine which conformation that satisfied the experimental NOE parameters the most, the NOESY spectrum of Sp1 was back-calculated from each conformation at mixing time 75 ms. Bush C A (1994) *Methods Enzymol* 240:446-59. The final models are in excellent agreement and are consistent with all intra- and interresidue NOE crosspeaks.

Conformation of Sp1. The overall shape of Sp1 can be described as a right-handed helix with eight residues per turn and a pitch of 19 Å. The amines (positive charges) are exposed on the outmost surface of the molecule and are in favorable positions for binding interactions. The calculated RMSD for the heavy atoms between structures in the MD simulation is of an order of 2 Å. This indicates that good convergence has been achieved. This successful convergence to a similar conformation is indicative of the precision of the restrained MD simulation. Most significant differences arise at the terminal regions and can probably be attributed to end fraying.

Comparing the Sp1 conformation with that of PS A2, it was observed that there was good superimposition of glycosidic oxygen atoms and amino groups. The glycosidic oxygen atoms of Sp CP1 could be superimposed to those of PS A2 with an RMSD value of 1.5 Å, indicating that these two ZPSs have essentially same backbone structure despite of different primary structures. The nitrogen atoms in the amines of Sp1 could be superimposed onto those of PS A2 with an RMSD value of 5.1 Å. Interestingly, the spatial arrangements of the amines of two polysaccharides showed a similar pattern. In both molecules, the amines point outwards and are arranged in a zigzag fashion. The average distance between the two adjacent amines in the middle of Sp1 4 RU is 15 Å, which is very close to that of PS A2.

Macroscopic Structure. One would expect the macroscopic/morphological features of Sp1 to form an extended fibrillar structure similar to cellulose and several polysaccharides that have been investigated by X-ray fiber diffraction. Sp1 dissolved in PBS at a concentration of 5 mg/mL was investigated by atomic force microscopy using a carbon nanoprobe. The image showed that Sp1 indeed forms filamentous structures.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim

1. An isolated immunomodulatory polymer comprising PS A2.

2. A pharmaceutical preparation which activates immune cells, comprising:
    an effective amount, for activating immune cells, of an isolated immunomodulatory polymer according to claim 1; and
    a pharmaceutically acceptable carrier.

* * * * *

UNITED STATES PATENT AND TRADEMARK OFFICE
CERTIFICATE OF CORRECTION

PATENT NO. : 7,629,330 B2
APPLICATION NO. : 10/432406
DATED : December 8, 2009
INVENTOR(S) : Julia Ying Wang et al.

It is certified that error appears in the above-identified patent and that said Letters Patent is hereby corrected as shown below:

Title Page, Item (75), Inventor "Ying Wang" should read "Julia Ying Wang"

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,629,330 B2 | Page 1 of 1 |
| APPLICATION NO. | : 10/432406 | |
| DATED | : December 8, 2009 | |
| INVENTOR(S) | : Ying Wang et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 595 days.

should read (*) Notice: Subject to any disclaimer, the term of this patent is extended or adjusted under 35 U.S.C. 154(b) by 1,182 days.

Signed and Sealed this

Third Day of August, 2010

David J. Kappos
*Director of the United States Patent and Trademark Office*